United States Patent
Marchand et al.

(10) Patent No.: US 10,765,731 B2
(45) Date of Patent: Sep. 8, 2020

(54) FUSION OF HETEROOLIGOMERIC MYCOBACTERIAL ANTIGENS

(71) Applicant: TRANSGENE SA, Illkirch Graffenstaden (FR)

(72) Inventors: Jean-Baptiste Marchand, Obernai (FR); Nathalie Silvestre, Ergersheim (FR); François Penin, Decines (FR)

(73) Assignee: TRANSGENE SA, Illkirch Graffenstaden (FR)

( * ) Notice: Subject to any disclaimer, the term of this patent is extended or adjusted under 35 U.S.C. 154(b) by 0 days.

(21) Appl. No.: 15/110,514

(22) PCT Filed: Jan. 9, 2015

(86) PCT No.: PCT/EP2015/050344
§ 371 (c)(1),
(2) Date: Jul. 8, 2016

(87) PCT Pub. No.: WO2015/104380
PCT Pub. Date: Jul. 16, 2015

(65) Prior Publication Data
US 2016/0331823 A1 Nov. 17, 2016

(30) Foreign Application Priority Data

Jan. 9, 2014 (EP) ..................................... 14305030

(51) Int. Cl.
*A61K 39/00* (2006.01)
*A61K 39/02* (2006.01)
*A61K 39/04* (2006.01)
*C07H 21/00* (2006.01)
*C07K 14/35* (2006.01)
*C07K 16/12* (2006.01)
*A61K 45/06* (2006.01)

(52) U.S. Cl.
CPC .............. *A61K 39/04* (2013.01); *A61K 45/06* (2013.01); *C07K 14/35* (2013.01); *C07K 16/1289* (2013.01); *A61K 2039/5256* (2013.01); *A61K 2039/53* (2013.01); *A61K 2039/57* (2013.01); *C07K 2317/34* (2013.01); *C07K 2319/00* (2013.01); *C07K 2319/035* (2013.01); *C12N 2710/24141* (2013.01)

(58) Field of Classification Search
CPC ........ A61K 39/00; A61K 39/02; A61K 39/04; C07H 21/00
USPC ......... 424/9.1, 9.2, 93.1, 93.2, 184.1, 185.1, 424/192.1, 234.1, 248.1
See application file for complete search history.

(56) References Cited

U.S. PATENT DOCUMENTS

| | | |
|---|---|---|
| 6,328,978 B1 | 12/2001 | Watson et al. |
| 2006/0024332 A1 | 2/2006 | Waters et al. |
| 2008/0199493 A1* | 8/2008 | Picker ............... A61K 39/04 424/208.1 |
| 2009/0068197 A1 | 3/2009 | Steyn et al. |
| 2009/0186048 A1 | 7/2009 | Aagaard et al. |
| 2010/0129391 A1 | 5/2010 | Reed et al. |
| 2010/0310585 A1 | 12/2010 | Agger et al. |
| 2011/0183342 A1 | 7/2011 | Lewinsohn et al. |
| 2012/0114687 A1* | 5/2012 | Aagard ............... A61K 39/04 424/190.1 |
| 2015/0165014 A1 | 6/2015 | Tupin et al. |

FOREIGN PATENT DOCUMENTS

| | | |
|---|---|---|
| CN | 101538578 A | 9/2009 |
| CN | 101900727 A | 12/2010 |
| CN | 102692509 A | 9/2012 |
| CN | 102719438 A | 10/2012 |
| CN | 103204945 A | 7/2013 |
| CN | 103333251 A | 10/2013 |
| CN | 103386128 A | 11/2013 |
| JP | 2015-536309 A | 12/2015 |
| JP | 2016-529223 A | 9/2016 |
| WO | WO 03/000721 A2 | 1/2003 |
| WO | WO 03/004520 A2 | 1/2003 |

(Continued)

OTHER PUBLICATIONS

Waters, W.R., et al. Clinical and Diagnostic Laboratory Immunology, vol. 11, No. 4, pp. 729-735, Jul. 2004.*
Aagaard, C. et al., "Protection and Polyfunctional T Cells Induced by Ag85B-TB10.4/IC31® against *Mycobacterium tuberculosis* Is Highly Dependent on the Antigen Dose," *PLOS One*, 4:1-8, 2009.
Acosta, A. et al, "The Importance of Animal Models in Tuberculosis Vaccine Development," *Malays J Med Sci*, 18:5-12, 2011.

(Continued)

*Primary Examiner* — Rodney P Swartz
(74) *Attorney, Agent, or Firm* — Finnegan, Henderson, Farabow, Garrett & Dunner, L.L.P.

(57) ABSTRACT

The present invention relates generally to novel immunogenic combinations comprising or encoding at least two heterooligomeric mycobacterial antigens and preferably a fusion polypeptide comprising said two heterooligomeric mycobacterial antigens, where the mycobacterial antigens are selected from the group of Esx, PE and PPE antigens of a *Mycobacterium* species, particularly a *Mycobacterium* of the tuberculosis complex such as *Mycobacterium tuberculosis* (Mtb). The present invention also relates to vectors, host cells and compositions comprising or encoding said immunogenic combination as well as to methods for expressing and producing it. The present invention also relates to methods of using said immunogenic combination, fusion polypeptide, vector, host cell, composition particularly for inducing or stimulating an immune response with the goal of providing a protective response against a *Mycobacterium* infection or any disease caused by or associated with a *Mycobacterium* infection.

23 Claims, 2 Drawing Sheets
Specification includes a Sequence Listing.

(56) References Cited

FOREIGN PATENT DOCUMENTS

| WO | WO 03/035681 A2 | 5/2003 |
| WO | WO 2004/006952 A2 | 1/2004 |
| WO | WO 2005/061534 A2 | 7/2005 |
| WO | WO2006026404 A2 * | 3/2006 |
| WO | WO 2006/104389 A1 | 10/2006 |
| WO | WO 2006/136162 A3 | 12/2006 |
| WO | WO 2008/124647 A2 | 10/2008 |
| WO | WO 2009/064825 A2 | 5/2009 |
| WO | WO 2010/034974 A3 | 4/2010 |
| WO | WO 2011/141451 A1 | 11/2011 |
| WO | WO 2011/144951 A1 | 11/2011 |
| WO | WO 2012/031752 A2 | 3/2012 |
| WO | WO 2012/057904 A1 | 5/2012 |
| WO | WO 2012/129227 A1 | 9/2012 |
| WO | WO 2014/009433 A1 | 1/2014 |
| WO | WO 2014/009438 A2 | 1/2014 |
| WO | WO 2014063704 A2 | 5/2014 |
| WO | WO 2014210018 A1 | 12/2014 |

OTHER PUBLICATIONS

Andersen, P. et al., "Tuberculosis Vaccines—An Update," *Nature*, 5:484, 2007.

Bertholet, S. et al., "Identification of Human T Cell Antigens for the Development of Vaccines Against *Mycobacterium tuberculosis*," *J. Immunol.*, 181:7948-7957, 2008.

Bertholet, S. et al., "A Defined Tuberculosis Vaccine Candidate Boosts BCG and Protects Against Multidrug Resistant *Mycobacterium tuberculosis*," *Sci. Transl. Med.*, 2:53ra74, 2010.

Brennan, M.J. et al., "A Rational Vaccine Pipeline for Tuberculosis," *Int J Tuberc Lung Dis*, 16:1566-1573, 2012.

Cayabyab, M.J. et al., "Current and Novel Approaches to Vaccine Development Against Tuberculosis," *Cel. & Infec. Microbiol.*, 2:1-16, 2012.

Cole, S.T. et al., "Deciphering the Biology of *Mycobacterium tuberculosis* from the Complete Genome Sequence," *Nature*, 393:537-44, 1998.

Commandeur, S. et al., "Identification of Human T-Cell Responses to *Mycobacterium tuberculosis* Resuscitation-Promoting Factors in Long-Term Latently Infected Individuals," *Clin. & Vacc. Immunol.*, 18:676-683, 2011.

Goonetilleke, N.P. et al., "Enhanced Immunogenicity and Protective Efficacy Against *Mycobacterium tuberculosis* of Bacille Calmette-Guerin Vaccine Using Mucosal Administration and Boosting with a Recombinant Modified Vaccinia Virus Ankara," *J Immunol*, 171:1602-1609, 2003.

Ilghari, D. et al., "Solution Structure of the *Mycobacterium tuberculosis* EsxG•EsxH Complex," *J Biol Chem*, 286:29993-30002, 2011.

International Search Report PCT/EP2051/050344 dated Jun. 9, 2015.

Kana, G.D. et al., "The Resuscitation-Promoting Factors of *Mycobacterium tuberculosis* Are Required for Virulence and Resuscitation From Dormancy but are Collectively Dispensable for Growth In Vitro," *Mol Microbiol*, 67:672-684, 2008.

Mehra, A. et al., "*Mycobacterium tuberculosis* Type VII Secreted Effector EsxH Targets Host ESCRT to Impair Trafficking," *PLOS*, 9:1-13, 2013.

Ottenhoff, T.H. et al., "Vaccines against Tuberculosis: Where Are We and Where Do We Need to Go," *PLOS*, 8:1-12, 2012.

Perez de Val, B. et al., "A Multi-Antigenic Adenoviral-Vectored Vaccine Improves BCG-Induced Protection of Goats against Pulmonary Tuberculosis Infection and Prevents Disease Progression," *PLOS*, 8:1-12, 2013.

Riley, R. et al., "Identifying Cognate Binding Pairs among a Large Set of Paralogs: The Case of PE/PPE Proteins of *Mycobacterium tuberculosis*," *PLOS*, 4:1-13, 2008.

Rook, G.A.W. et al., Immunotherapeutics for Tuberculosis in Experimental Animals: *Perspective*, 196:191-8, 2007.

Singh, S. et al., "Immunogenic Potential of Latency Associated Antigens Against *Mycobacterium tuberculosis*," *Vaccine*, 2013.

Strong, M. et al., "Toward the structural genomics of complexes: Crystal structure of a PE/PPE protein complex from *Mycobacterium tuberculosis*," *PNAS*, 103:8060-8065, 2006.

Von Eschen, K. et al., "The candidate tuberculosis vaccine Mtb72F/AS02A," *Human Vaccines*, 5:475-482, 2009.

Yeremeev, V.V et al, "Proteins of the Rpf Family: Immune Cell Reactivity and Vaccination Efficacy against Tuberculosis in Mice," *Infec& Immun*, 71:4789-4794, 2003.

Zhang, F. et al., "Multiple antigen-presenting system (MAPS) to induce comprehensive B- and T-cell immunity," *PNAS*, 110:13564-13569, 2013.

Kosturko, et al., "Polar Encapsidation of Adenovirus DNA: Cloning and DNA Sequence of the Left End of Adenovirus Type 3," J. Virol., 1982, vol. 43, pp. 1132-1137.

Moss, "Genetically engineered poxviruses for recombinant gene expression, vaccination, and safety," Proc. Natl. Acad. Sci. USA, 1996, vol. 93, pp. 11341-11348.

Upton, et al., "Poxvirus Orthologous Clusters: toward Defining the Minimum Essential Poxvirus Genome," J. Virol., 2003, vol. 77, pp. 7590-7600.

Du, et al., "Vaccinia virus DNA replication: Two hundred base pairs of telomeric sequence confer optimal replication efficiency on minichromosome templates," Proc. Natl. Acad. Sci. USA, 1996, pp. 9693-9698.

Menon, et al., "Mycobacterial ESAT-6 Protein Enhances Mouse IFN-γ Responses to Mycoplasma hyopneumoniae P71 Protein" J. Interferon Cytokine Res., 2002, vol. 22, pp. 807-813.

User Guide: Invitrogen TA Cloning® Kit, Life Technologies, dated Jun. 5, 2013.

User Manual: pTrcHis A, B, and C Vectors for Expression of Recombinant Proteins Containing N-Terminal 6xHis Tags in *E. coli*, Version H, Invitrogen, dated Oct. 20, 2008.

* cited by examiner

(a) MVATGN33.1

(b) MVATG18379 and MVATG18598

(a) MVATGN33.1

(b) MVATG18597, MVATG18633 and MVATG18377

SEQUENCE LISTING

<160> NUMBER OF SEQ ID NOS: 33

<210> SEQ ID NO 1
<211> LENGTH: 208
<212> TYPE: PRT
<213> ORGANISM: artificial sequence
<220> FEATURE:
<223> OTHER INFORMATION: fusion between CFP10 and its partner ESAT-6

<400> SEQUENCE: 1

```
Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
            20                  25                  30

Glu Ser Thr Ala Gly Ser Leu Gln Gly Gln Trp Arg Gly Ala Ala Gly
        35                  40                  45

Thr Ala Ala Gln Ala Ala Val Val Arg Phe Gln Glu Ala Ala Asn Lys
    50                  55                  60

Gln Lys Gln Glu Leu Asp Glu Ile Ser Thr Asn Ile Arg Gln Ala Gly
65                  70                  75                  80

Val Gln Tyr Ser Arg Ala Asp Glu Glu Gln Gln Gln Ala Leu Ser Ser
                85                  90                  95

Gln Met Gly Phe Gly Pro Lys Gln Gly Glu Asp Asp Gly Ser Thr Gly
            100                 105                 110

Gly Pro Thr Glu Gln Gln Trp Asn Phe Ala Gly Ile Glu Ala Ala Ala
        115                 120                 125

Ser Ala Ile Gln Gly Asn Val Thr Ser Ile His Ser Leu Leu Asp Glu
    130                 135                 140

Gly Lys Gln Ser Leu Thr Lys Leu Ala Ala Ala Trp Gly Gly Ser Gly
145                 150                 155                 160

Ser Glu Ala Tyr Gln Gly Val Gln Gln Lys Trp Asp Ala Thr Ala Thr
                165                 170                 175

Glu Leu Asn Asn Ala Leu Gln Asn Leu Ala Arg Thr Ile Ser Glu Ala
            180                 185                 190

Gly Gln Ala Met Ala Ser Thr Glu Gly Asn Val Thr Gly Met Phe Ala
        195                 200                 205
```

<210> SEQ ID NO 2
<211> LENGTH: 205
<212> TYPE: PRT
<213> ORGANISM: artificial sequence
<220> FEATURE:
<223> OTHER INFORMATION: fusion between TB10.4 and its parner TB9.8
    (Rv0287)

<400> SEQUENCE: 2

```
Met Ser Gln Ile Met Tyr Asn Tyr Pro Ala Met Leu Gly His Ala Gly
1               5                   10                  15

Asp Met Ala Gly Tyr Ala Gly Thr Leu Gln Ser Leu Gly Ala Glu Ile
            20                  25                  30

Ala Val Glu Gln Ala Ala Leu Gln Ser Ala Trp Gln Gly Asp Thr Gly
        35                  40                  45

Ile Thr Tyr Gln Ala Trp Gln Ala Gln Trp Asn Gln Ala Met Glu Asp
    50                  55                  60

Leu Val Arg Ala Tyr His Ala Met Ser Ser Thr His Glu Ala Asn Thr
65                  70                  75                  80

Met Ala Met Met Ala Arg Asp Thr Ala Glu Ala Ala Lys Trp Gly Gly
                85                  90                  95
```

Gly Pro Lys Gln Gly Glu Asp Gly Ser Thr Gly Ser Leu Leu
            100                 105                 110

Asp Ala His Ile Pro Gln Leu Val Ala Ser Gln Ser Ala Phe Ala Ala
            115                 120                 125

Lys Ala Gly Leu Met Arg His Thr Ile Gly Gln Ala Glu Gln Ala Ala
130                 135                 140

Met Ser Ala Gln Ala Phe His Gln Gly Glu Ser Ser Ala Ala Phe Gln
145                 150                 155                 160

Ala Ala His Ala Arg Phe Val Ala Ala Ala Lys Val Asn Thr Leu
                165                 170                 175

Leu Asp Val Ala Gln Ala Asn Leu Gly Glu Ala Ala Gly Thr Tyr Val
            180                 185                 190

Ala Ala Asp Ala Ala Ala Ala Ser Thr Tyr Thr Gly Phe
            195                 200                 205

<210> SEQ ID NO 3
<211> LENGTH: 113
<212> TYPE: PRT
<213> ORGANISM: artificial sequence
<220> FEATURE:
<223> OTHER INFORMATION: mutant of Rv1813 antigen

<400> SEQUENCE: 3

Asp Ala His Leu Ala Asn Gly Ser Met Ser Glu Val Met Met Ser Glu
1               5                   10                  15

Ile Ala Gly Leu Pro Ile Pro Pro Ile Ile His Tyr Gly Ala Ile Ala
            20                  25                  30

Tyr Ala Pro Ser Gly Ala Ser Gly Lys Ala Trp His Gln Arg Thr Pro
        35                  40                  45

Ala Arg Ala Glu Gln Val Ala Leu Glu Lys Cys Gly Asp Lys Thr Cys
    50                  55                  60

Lys Val Val Ser Arg Phe Thr Arg Cys Gly Ala Val Ala Tyr Asn Gly
65                  70                  75                  80

Ser Lys Tyr Gln Gly Gly Thr Gly Leu Thr Arg Arg Ala Ala Glu Asp
                85                  90                  95

Asp Ala Val Asn Arg Leu Glu Gly Gly Arg Ile Val Asn Trp Ala Cys
            100                 105                 110

Asn

<210> SEQ ID NO 4
<211> LENGTH: 293
<212> TYPE: PRT
<213> ORGANISM: artificial sequence
<220> FEATURE:
<223> OTHER INFORMATION: mutant of Ag85B antigen

<400> SEQUENCE: 4

Gly Gly Ala Ala Thr Ala Gly Ala Phe Ser Arg Pro Gly Leu Pro Val
1               5                   10                  15

Glu Tyr Leu Gln Val Pro Ser Pro Ser Met Gly Arg Asp Ile Lys Val
            20                  25                  30

Gln Phe Gln Ser Gly Gly Asn Asn Ser Pro Ala Val Tyr Leu Leu Asp
        35                  40                  45

Gly Leu Arg Ala Gln Asp Asp Tyr Asn Gly Trp Asp Ile Asn Thr Pro
    50                  55                  60

Ala Phe Glu Trp Tyr Tyr Gln Ser Gly Leu Ser Ile Val Met Pro Val
65                  70                  75                  80

```
Gly Gly Gln Ser Ser Phe Tyr Ser Asp Trp Tyr Ser Pro Ala Cys Gly
                85                  90                  95

Lys Ala Gly Cys Gln Thr Tyr Lys Trp Glu Thr Phe Leu Thr Ser Glu
            100                 105                 110

Leu Pro Gln Trp Leu Ser Ala Asn Arg Ala Val Lys Pro Thr Gly Ser
        115                 120                 125

Ala Ala Ile Gly Leu Ser Met Ala Gly Ser Ser Ala Met Ile Leu Ala
    130                 135                 140

Ala Tyr His Pro Gln Gln Phe Ile Tyr Ala Gly Ser Leu Ser Ala Leu
145                 150                 155                 160

Leu Asp Pro Ser Gln Gly Met Gly Pro Ser Leu Ile Gly Leu Ala Met
                165                 170                 175

Gly Asp Ala Gly Gly Tyr Lys Ala Ala Asp Met Trp Gly Pro Ser Ser
            180                 185                 190

Asp Pro Ala Trp Glu Arg Asn Asp Pro Thr Gln Gln Ile Pro Lys Leu
        195                 200                 205

Val Ala Asn Asn Thr Arg Leu Trp Val Tyr Cys Gly Asn Gly Thr Pro
    210                 215                 220

Asn Glu Leu Gly Gly Ala Asn Ile Pro Ala Glu Phe Leu Glu Asn Phe
225                 230                 235                 240

Val Arg Ser Ser Asn Leu Lys Phe Gln Asp Ala Tyr Asn Ala Ala Gly
                245                 250                 255

Gly His Asn Ala Val Phe Asn Phe Pro Pro Asn Gly Thr His Ser Trp
            260                 265                 270

Glu Tyr Trp Gly Ala Gln Leu Asn Ala Met Lys Gly Asp Leu Gln Ser
        275                 280                 285

Ser Leu Gly Ala Gly
    290

<210> SEQ ID NO 5
<211> LENGTH: 22
<212> TYPE: PRT
<213> ORGANISM: artificial sequence
<220> FEATURE:
<223> OTHER INFORMATION: isolated cleavage site F2A of the foot and
      mouth disease virus

<400> SEQUENCE: 5

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 6
<211> LENGTH: 18
<212> TYPE: PRT
<213> ORGANISM: artificial sequence
<220> FEATURE:
<223> OTHER INFORMATION: isolated cleavage site 2A peptide of the Thosea
      asigna virus

<400> SEQUENCE: 6

Glu Gly Arg Gly Ser Leu Leu Thr Cys Gly Asp Val Glu Glu Asn Pro
1               5                   10                  15

Gly Pro

<210> SEQ ID NO 7
<211> LENGTH: 20
```

```
<212> TYPE: PRT
<213> ORGANISM: artificial sequence
<220> FEATURE:
<223> OTHER INFORMATION: isolated cleavge site 2A peptide of Equine
      rhinitis A virus

<400> SEQUENCE: 7

Gln Cys Thr Asn Tyr Ala Leu Leu Lys Leu Ala Gly Asp Val Glu Ser
1               5                   10                  15

Asn Pro Gly Pro
            20

<210> SEQ ID NO 8
<211> LENGTH: 357
<212> TYPE: PRT
<213> ORGANISM: artificial sequence
<220> FEATURE:
<223> OTHER INFORMATION: fusion of modified RpfB and RpfD resuscitation
      Mtb antigens

<400> SEQUENCE: 8

Met Thr Val Asp Gly Thr Ala Met Arg Val Thr Thr Met Lys Ser Arg
1               5                   10                  15

Val Ile Asp Ile Val Glu Glu Asn Gly Phe Ser Val Asp Asp Arg Asp
            20                  25                  30

Asp Leu Tyr Pro Ala Ala Gly Val Gln Val His Asp Ala Asp Thr Ile
        35                  40                  45

Val Leu Arg Arg Ser Arg Pro Leu Gln Ile Ser Leu Asp Gly His Asp
    50                  55                  60

Ala Lys Gln Val Trp Thr Thr Ala Ser Thr Val Asp Glu Ala Leu Ala
65                  70                  75                  80

Gln Leu Ala Met Thr Asp Thr Ala Pro Ala Ala Ala Ser Arg Ala Ser
                85                  90                  95

Arg Val Pro Leu Ser Gly Met Ala Leu Pro Val Val Ser Ala Lys Thr
            100                 105                 110

Val Gln Leu Asn Asp Gly Gly Leu Val Arg Thr Val His Leu Pro Ala
        115                 120                 125

Pro Asn Val Ala Gly Leu Leu Ser Ala Ala Gly Val Pro Leu Leu Gln
    130                 135                 140

Ser Asp His Val Val Pro Ala Ala Thr Ala Pro Ile Val Glu Gly Met
145                 150                 155                 160

Gln Ile Gln Val Thr Arg Asn Arg Ile Lys Lys Val Thr Glu Arg Leu
                165                 170                 175

Pro Leu Pro Pro Asn Ala Arg Arg Val Glu Asp Pro Glu Met Asn Met
            180                 185                 190

Ser Arg Glu Val Val Glu Asp Pro Gly Val Pro Gly Thr Gln Asp Val
        195                 200                 205

Thr Phe Ala Val Ala Glu Val Asn Gly Val Glu Thr Gly Arg Leu Pro
    210                 215                 220

Val Ala Asn Val Val Val Thr Pro Ala His Glu Ala Val Val Arg Val
225                 230                 235                 240

Gly Thr Lys Pro Gly Thr Glu Val Pro Pro Val Ile Asp Gly Ser Ile
                245                 250                 255

Trp Asp Ala Ile Ala Gln Cys Lys Ser Gly Gly Asn Trp Ala Ala Asn
            260                 265                 270

Thr Gly Asn Gly Leu Tyr Gly Gly Leu Gln Ile Ser Gln Ala Ala Trp
        275                 280                 285
```

```
Asp Ser Asn Gly Gly Val Gly Ser Pro Ala Ala Ser Pro Gln Gln
    290                 295                 300

Gln Ile Glu Val Ala Asp Asn Ile Met Lys Thr Ala Gly Pro Gly Ala
305                 310                 315                 320

Trp Pro Lys Cys Ser Cys Ser Gln Gly Asp Ala Pro Leu Gly Ser
                325                 330                 335

Leu Thr His Ile Leu Thr Phe Leu Ala Ala Glu Thr Gly Gly Cys Ser
                340                 345                 350

Gly Ser Arg Asp Asp
            355

<210> SEQ ID NO 9
<211> LENGTH: 457
<212> TYPE: PRT
<213> ORGANISM: artificial sequence
<220> FEATURE:
<223> OTHER INFORMATION: fusion of Rv2626 with Ag85B** Mtb antigens with
      F2A cleavage site in between

<400> SEQUENCE: 9

Met Thr Thr Ala Arg Asp Ile Met Asn Ala Gly Val Thr Cys Val Gly
1               5                   10                  15

Glu His Glu Thr Leu Thr Ala Ala Gln Tyr Met Arg Glu His Asp
                20                  25                  30

Ile Gly Ala Leu Pro Ile Cys Gly Asp Asp Arg Leu His Gly Met
            35                  40                  45

Leu Thr Asp Arg Asp Ile Val Ile Lys Gly Leu Ala Ala Gly Leu Asp
50                  55                  60

Pro Asn Thr Ala Thr Ala Gly Glu Leu Ala Arg Asp Ser Ile Tyr Tyr
65                  70                  75                  80

Val Asp Ala Asn Ala Ser Ile Gln Glu Met Leu Asn Val Met Glu Glu
                85                  90                  95

His Gln Val Arg Arg Val Pro Val Ile Ser Glu His Arg Leu Val Gly
                100                 105                 110

Ile Val Thr Glu Ala Asp Ile Ala Arg His Leu Pro Glu His Ala Ile
            115                 120                 125

Val Gln Phe Val Lys Ala Ile Cys Ser Pro Met Ala Leu Ala Ser Gly
    130                 135                 140

Ser Gly Glu Gly Arg Gly Ser Leu Leu Thr Cys Gly Asp Val Glu Glu
145                 150                 155                 160

Asn Pro Gly Pro Gly Ala Ala Thr Ala Gly Ala Phe Ser Arg Pro
                165                 170                 175

Gly Leu Pro Val Glu Tyr Leu Gln Val Pro Ser Pro Ser Met Gly Arg
            180                 185                 190

Asp Ile Lys Val Gln Phe Gln Ser Gly Gly Asn Ser Pro Ala Val
    195                 200                 205

Tyr Leu Leu Asp Gly Leu Arg Ala Gln Asp Asp Tyr Asn Gly Trp Asp
    210                 215                 220

Ile Asn Thr Pro Ala Phe Glu Trp Tyr Tyr Gln Ser Gly Leu Ser Ile
225                 230                 235                 240

Val Met Pro Val Gly Gly Gln Ser Ser Phe Tyr Ser Asp Trp Tyr Ser
                245                 250                 255

Pro Ala Cys Gly Lys Ala Gly Cys Gln Thr Tyr Lys Trp Glu Thr Phe
            260                 265                 270

Leu Thr Ser Glu Leu Pro Gln Trp Leu Ser Ala Asn Arg Ala Val Lys
    275                 280                 285
```

```
Pro Thr Gly Ser Ala Ala Ile Gly Leu Ser Met Ala Gly Ser Ser Ala
    290                 295                 300

Met Ile Leu Ala Ala Tyr His Pro Gln Gln Phe Ile Tyr Ala Gly Ser
305                 310                 315                 320

Leu Ser Ala Leu Leu Asp Pro Ser Gln Gly Met Gly Pro Ser Leu Ile
                325                 330                 335

Gly Leu Ala Met Gly Asp Ala Gly Gly Tyr Lys Ala Ala Asp Met Trp
                340                 345                 350

Gly Pro Ser Ser Asp Pro Ala Trp Glu Arg Asn Asp Pro Thr Gln Gln
            355                 360                 365

Ile Pro Lys Leu Val Ala Asn Asn Thr Arg Leu Trp Val Tyr Cys Gly
    370                 375                 380

Asn Gly Thr Pro Asn Glu Leu Gly Gly Ala Asn Ile Pro Ala Glu Phe
385                 390                 395                 400

Leu Glu Asn Phe Val Arg Ser Ser Asn Leu Lys Phe Gln Asp Ala Tyr
                405                 410                 415

Asn Ala Ala Gly Gly His Asn Ala Val Phe Asn Phe Pro Pro Asn Gly
                420                 425                 430

Thr His Ser Trp Glu Tyr Trp Gly Ala Gln Leu Asn Ala Met Lys Gly
            435                 440                 445

Asp Leu Gln Ser Ser Leu Gly Ala Gly
    450                 455

<210> SEQ ID NO 10
<211> LENGTH: 436
<212> TYPE: PRT
<213> ORGANISM: artificial sequence
<220> FEATURE:
<223> OTHER INFORMATION: fusion of Rv2626 and Ag85B** Mtb antigens

<400> SEQUENCE: 10

Met Thr Thr Ala Arg Asp Ile Met Asn Ala Gly Val Thr Cys Val Gly
1               5                   10                  15

Glu His Glu Thr Leu Thr Ala Ala Gln Tyr Met Arg Glu His Asp
                20                  25                  30

Ile Gly Ala Leu Pro Ile Cys Gly Asp Asp Arg Leu His Gly Met
            35                  40                  45

Leu Thr Asp Arg Asp Ile Val Ile Lys Gly Leu Ala Ala Gly Leu Asp
    50                  55                  60

Pro Asn Thr Ala Thr Ala Gly Glu Leu Ala Arg Asp Ser Ile Tyr Tyr
65                  70                  75                  80

Val Asp Ala Asn Ala Ser Ile Gln Glu Met Leu Asn Val Met Glu Glu
                85                  90                  95

His Gln Val Arg Arg Val Pro Val Ile Ser Glu His Arg Leu Val Gly
                100                 105                 110

Ile Val Thr Glu Ala Asp Ile Ala Arg His Leu Pro Glu His Ala Ile
            115                 120                 125

Val Gln Phe Val Lys Ala Ile Cys Ser Pro Met Ala Leu Ala Ser Gly
    130                 135                 140

Gly Ala Ala Thr Ala Gly Ala Phe Ser Arg Pro Gly Leu Pro Val Glu
145                 150                 155                 160

Tyr Leu Gln Val Pro Ser Pro Ser Met Gly Arg Asp Ile Lys Val Gln
                165                 170                 175

Phe Gln Ser Gly Gly Asn Asn Ser Pro Ala Val Tyr Leu Leu Asp Gly
                180                 185                 190
```

Leu Arg Ala Gln Asp Asp Tyr Asn Gly Trp Asp Ile Asn Thr Pro Ala
        195                 200                 205

Phe Glu Trp Tyr Tyr Gln Ser Gly Leu Ser Ile Val Met Pro Val Gly
210                 215                 220

Gly Gln Ser Ser Phe Tyr Ser Asp Trp Tyr Ser Pro Ala Cys Gly Lys
225                 230                 235                 240

Ala Gly Cys Gln Thr Tyr Lys Trp Glu Thr Phe Leu Thr Ser Glu Leu
            245                 250                 255

Pro Gln Trp Leu Ser Ala Asn Arg Ala Val Lys Pro Thr Gly Ser Ala
        260                 265                 270

Ala Ile Gly Leu Ser Met Ala Gly Ser Ser Ala Met Ile Leu Ala Ala
        275                 280                 285

Tyr His Pro Gln Gln Phe Ile Tyr Ala Gly Ser Leu Ser Ala Leu Leu
        290                 295                 300

Asp Pro Ser Gln Gly Met Gly Pro Ser Leu Ile Gly Leu Ala Met Gly
305                 310                 315                 320

Asp Ala Gly Gly Tyr Lys Ala Ala Asp Met Trp Gly Pro Ser Ser Asp
            325                 330                 335

Pro Ala Trp Glu Arg Asn Asp Pro Thr Gln Gln Ile Pro Lys Leu Val
        340                 345                 350

Ala Asn Asn Thr Arg Leu Trp Val Tyr Cys Gly Asn Gly Thr Pro Asn
        355                 360                 365

Glu Leu Gly Gly Ala Asn Ile Pro Ala Glu Phe Leu Glu Asn Phe Val
        370                 375                 380

Arg Ser Ser Asn Leu Lys Phe Gln Asp Ala Tyr Asn Ala Ala Gly Gly
385                 390                 395                 400

His Asn Ala Val Phe Asn Phe Pro Pro Asn Gly Thr His Ser Trp Glu
            405                 410                 415

Tyr Trp Gly Ala Gln Leu Asn Ala Met Lys Gly Asp Leu Gln Ser Ser
        420                 425                 430

Leu Gly Ala Gly
        435

<210> SEQ ID NO 11
<211> LENGTH: 235
<212> TYPE: PRT
<213> ORGANISM: artificial sequence
<220> FEATURE:
<223> OTHER INFORMATION: fusion of Rv3407 and Rv1813** Mtb antigens with
      E2A cleavage site in between

<400> SEQUENCE: 11

Met Arg Ala Thr Val Gly Leu Val Glu Ala Ile Gly Ile Ar

```
            100                 105                 110
Ala Gly Asp Val Glu Ser Asn Pro Gly Pro Asp Ala His Leu Ala Asn
        115                 120                 125
Gly Ser Met Ser Glu Val Met Met Ser Glu Ile Ala Gly Leu Pro Ile
    130                 135                 140
Pro Pro Ile Ile His Tyr Gly Ala Ile Ala Tyr Ala Pro Ser Gly Ala
145                 150                 155                 160
Ser Gly Lys Ala Trp His Gln Arg Thr Pro Ala Arg Ala Glu Gln Val
                165                 170                 175
Ala Leu Glu Lys Cys Gly Asp Lys Thr Cys Lys Val Val Ser Arg Phe
            180                 185                 190
Thr Arg Cys Gly Ala Val Ala Tyr Asn Gly Ser Lys Tyr Gln Gly Gly
        195                 200                 205
Thr Gly Leu Thr Arg Arg Ala Ala Glu Asp Asp Ala Val Asn Arg Leu
    210                 215                 220
Glu Gly Gly Arg Ile Val Asn Trp Ala Cys Asn
225                 230                 235

<210> SEQ ID NO 12
<211> LENGTH: 212
<212> TYPE: PRT
<213> ORGANISM: artificial sequence
<220> FEATURE:
<223> OTHER INFORMATION: fusion of Rv3407 and Rv1813* Mtb antigens

<400> SEQUENCE: 12

Met Arg Ala Thr Val Gly Leu Val Glu Ala Ile Gly Ile Arg Glu Leu
1               5                   10                  15
Arg Gln His Ala Ser Arg Tyr Leu Ala Arg Val Glu Ala Gly Glu Glu
            20                  25                  30
Leu Gly Val Thr Asn Lys Gly Arg Leu Val Ala Arg Leu Ile Pro Val
        35                  40                  45
Gln Ala Ala Glu Arg Ser Arg Glu Ala Leu Ile Glu Ser Gly Val Leu
    50                  55                  60
Ile Pro Ala Arg Arg Pro Gln Asn Leu Leu Asp Val Thr Ala Glu Pro
65                  70                  75                  80
Ala Arg Gly Arg Lys Arg Thr Leu Ser Asp Val Leu Asn Glu Met Arg
                85                  90                  95
Asp Glu Gln Asp Ala His Leu Ala Asn Gly Ser Met Ser Glu Val Met
            100                 105                 110
Met Ser Glu Ile Ala Gly Leu Pro Ile Pro Pro Ile Ile His Tyr Gly
        115                 120                 125
Ala Ile Ala Tyr Ala Pro Ser Gly Ala Ser Gly Lys Ala Trp His Gln
    130                 135                 140
Arg Thr Pro Ala Arg Ala Glu Gln Val Ala Leu Glu Lys Cys Gly Asp
145                 150                 155                 160
Lys Thr Cys Lys Val Val Ser Arg Phe Thr Arg Cys Gly Ala Val Ala
                165                 170                 175
Tyr Asn Gly Ser Lys Tyr Gln Gly Gly Thr Gly Leu Thr Arg Arg Ala
            180                 185                 190
Ala Glu Asp Asp Ala Val Asn Arg Leu Glu Gly Gly Arg Ile Val Asn
        195                 200                 205
Trp Ala Cys Asn
    210
```

<210> SEQ ID NO 13
<211> LENGTH: 637
<212> TYPE: DNA
<213> ORGANISM: artificial sequence
<220> FEATURE:
<223> OTHER INFORMATION: nt sequence encoding the fusion of CFP10 with its partner ESAT6

<400> SEQUENCE: 13

```
accatggccg agatgaagac cgatgccgcc accctggctc aggaagccgg caacttcgag      60
agaatcagcg gcgacctgaa acccagatcg accaggtgg aaagcaccgc cggatctctg     120
cagggacagt ggcggggagc tgctggaaca gctgctcagg ctgctgtcgt gcggtttcag     180
gaagctgcca acaagcagaa gcaggaactg gacgagatca gcaccaacat ccggcaggcc     240
ggcgtgcagt acagcagagc cgatgaggaa cagcagcagg ccctgtccag ccagatgggc     300
tttggaccta agcagggcga ggatgatggc tctacaggcg ccctaccga gcagcagtgg     360
aacttcgccg gaattgaggc cgctgccagc gccatccagg gcaacgtgac atccatccac     420
agcctgctgg acgagggcaa gcagagcctg acaaaactgg ctgctgcctg gggcggctct     480
ggctctgaag cttatcaggg cgtgcagcag aagtgggacg ccaccgccac cgagctgaac     540
aacgccctgc agaacctggc ccggacaatc tctgaagccg acaggccat ggccagcacc      600
gagggcaatg tgaccggcat gtttgcctaa ttttgt                               637
```

<210> SEQ ID NO 14
<211> LENGTH: 628
<212> TYPE: DNA
<213> ORGANISM: artificial sequence
<220> FEATURE:
<223> OTHER INFORMATION: nt sequence coding for the fusion of TB10.4 Mtb antigen with its partner TB9.8 (Rv0287)

<400> SEQUENCE: 14

```
accatgagcc agatcatgta caactacccc gccatgctgg gccacgccgg cgatatggct      60
ggatatgccg gcacactgca gagcctgggt gccgagattg ccgtggaaca ggctgccctc     120
cagtctgcct ggcagggcga taccggcatc acataccagg cttggcaggc ccagtggaac     180
caggccatgg aagatctcgt gcgggcctac acgccatga gcagcacaca cgaggccaac      240
accatggcca tgatggcccg ggatacagcc gaggccgcta gtggggagg aggccccaaa     300
caaggagaag atgacggcag caccggagga agtctgctcg acgccacat ccctcagctc      360
gtggctagcc agtctgcctt tgccgccaaa gccggcctga tgagacacac cattggccag     420
gccgaacagg ccgccatgtc tgcccaggct tttcaccagg cgaaagcag cgccgccttt      480
caggccgccc atgccagatt tgtggccgct gccgctaaag tgaacaccct cctggacgtg     540
gcccaggcca atctgggaga agccgccgga acttacgtgg ccgcagatgc cgctgctgcc     600
agcacctaca caggcttcta gttttct                                         628
```

<210> SEQ ID NO 15
<211> LENGTH: 1084
<212> TYPE: DNA
<213> ORGANISM: artificial sequence
<220> FEATURE:
<223> OTHER INFORMATION: nt sequence coding for the fusion of mutant RpfB and RpfD Mtb antigens

<400> SEQUENCE: 15

```
accatgaccg tggacggcac cgccatgaga gtgaccacca tgaagtccag agtgatcgac      60
atcgtggaag agaacggctt cagcgtggac gaccgggacg acctgtatcc tgctgctgga     120
```

```
gtgcaggtcc acgacgccga tacaatcgtg ctgcggagaa gcagacccct gcagatcagc      180
ctggatggcc acgacgccaa gcaggtctgg accacagcca gcacagtgga tgaagccctg      240
gcccagctgg ccatgaccga tacagctcca gccgccgcta gcagagctag cagagtgcct      300
ctgtctggca tggccctgcc tgtggtgtct gccaagaccg tgcagctgaa cgatggcggc      360
ctcgtgcgga cagtgcatct gcctgctcct aatgtggccg gcctgctgtc tgcagcaggc      420
gtgccactgc tgcagagcga tcatgtggtg cctgccgcca cagcccctat cgtggaaggc      480
atgcagatcc aggtcacacg gaaccggatc aagaaagtga ccgagcggct gcccctgcct      540
cccaacgcta agagtggaa agatcccgag atgaacatga gcagagaggt ggtcgaggac      600
cctggcgtgc aggcacaca ggatgtgaca ttcgccgtgg ccgaagtgaa cggcgtggaa      660
accggcagac tgcccgtggc caatgtggtg gtcacaccag cccatgaggc cgtcgtcaga      720
gtgggcacaa agcctggcac agaggtgcca cccgtgatcg acggcagcat ctgggatgcc      780
attgcccagt gcaagagcgg cggaaactgg ccgccaata ccggcaatgg cctctatggc      840
ggcctgcaga tctctcaggc cgcctgggat tctaatggcg gcgtgggatc tcctgccgct      900
gcctctccac agcagcagat cgaggtggcc gacaacatca tgaagacagc cggacctggc      960
gcctggccca gtgtagcag ttgttctcag ggcgacgccc tctgggcag cctgacacac     1020 atcctgacat ttctggccgc cgagacaggc ggatgtagcg gctctagaga tgactagttt     1080
ttct                                                                  1084

<210> SEQ ID NO 16
<211> LENGTH: 1384
<212> TYPE: DNA
<213> ORGANISM: artificial sequence
<220> FEATURE:
<223> OTHER INFORMATION: nt sequence coding for the fusion of Rv2626
      with Ag85B** Mtb antigens with peptide 2A cleavage site in between

<400> SEQUENCE: 16
accatgacaa ccgccagaga catcatgaac gccggcgtga cctgtgtggg cgagcacgag       60
acactgacag ccgccgctca gtacatgaga gagcacgaca tcggcgcccct gcccatctgc     120 ggcgacgatg atagactgca cggcatgctg accgaccggg acatcgtgat caagggcctg     180
gctgctggcc tggaccccaa tactgctaca gctggcgagc tggcaagaga cagcatctac     240
tacgtggacg ccaacgccag catccaggaa atgctgaacg tgatggaaga caccaggtc      300 cgacgggtgc ccgtgatcag cgaacacaga ctcgtgggca tcgtgaccga ggccgatatc     360
gccagacatc tgcccgagca cgccatcgtg cagttcgtga aggccatctg cagccccatg     420
gccctggcct ctggcagcgg agagggcaga ggcagcctgc tgacatgtgg tgacgtagag     480
gagaatccag gacctggcgg agctgctaca gccggcgcct ctctagacc tggcctgccc     540 gtggaatacc tgcaggtccc aagcccagc atgggccggg atatcaaggt gcagtttcag     600
agcggcggca caacagccc tgccgtgtat ctgctggatg gcctgagagc caggacgac     660 tacaacggct gggacatcaa cacccctgcc ttcgagtggt actaccagag cggcctgtcc     720
atcgtgatgc ctgtgggcgg ccagagcagc ttctacagcg actggtacag ccccgcctgt     780
ggcaaagccg gctgccagac ctacaagtgg gagacattcc tgacctccga gctgcccag     840 tggctgagcg ccaatagagc cgtgaagcct acaggctctg ccgccatcgg actgagcatg     900
gccggaagct ctgccatgat cctggccgcc tatcacccct cagcagttcat ctacgccggc     960 agcctgtctg ccctgctgga cccttctcag ggcatgggcc cttctctgat cggactggct    1020
```

| atgggcgacg ctggcggata caaggccgcc gatatgtggg gccctagcag cgatcctgcc | 1080 |
| tgggagagaa acgaccccac ccagcagatc cccaagctgg tggccaacaa cacccggctg | 1140 |
| tgggtgtact gcggcaacgg caccoctaat gaactgggcg agccaatat ccccgccgag | 1200 |
| ttcctggaaa acttcgtgcg gagcagcaac ctgaagttcc aggatgccta caacgccgct | 1260 |
| ggcggccaca cgccgtgtt caacttccct cccaatggca cccacagctg ggagtactgg | 1320 |
| ggagcccagc tgaacgccat gaagggcgat ctgcagtcct ctctgggagc cggctaattt | 1380 |
| ttct | 1384 |

<210> SEQ ID NO 17
<211> LENGTH: 1321
<212> TYPE: DNA
<213> ORGANISM: artificial sequence
<220> FEATURE:
<223> OTHER INFORMATION: nt sequence coding for the fusion of Rv2626
    with Ag85B** Mtb antigens

<400> SEQUENCE: 17

| accatgacaa ccgccagaga catcatgaac gccggcgtga cctgtgtggg cgagcacgag | 60 |
| acactgcacg ccgccgctca gtacatgaga gagcacgaca tcggcgccct gcccatctgc | 120 |
| ggcgacgatg atagactgca cggcatgctg accgaccggg acatcgtgat caagggcctg | 180 |
| gctgctggcc tggaccccaa tactgctaca gctggcgagc tggcaagaga cagcatctac | 240 |
| tacgtggacg ccaacgccag catccaggaa atgctgaacg tgatggaaga caccaggtc | 300 |
| cgacgggtgc ccgtgatcag cgaacacaga ctcgtgggca tcgtgaccga ggccgatatc | 360 |
| gccagacatc tgcccgagca cgccatcgtg cagttcgtga aggccatctg cagccccatg | 420 |
| gccctggcct ctggcggagc tgctacagcc ggcgccttct ctagacctgg cctgcccgtg | 480 |
| gaatacctgc aggtcccaag ccccagcatg gccgggata tcaaggtgca gtttcagagc | 540 |
| ggcggcaaca cagccctgc cgtgtatctg ctggatggcc tgagagccca ggacgactac | 600 |
| aacggctggg acatcaacac ccctgccttc gagtggtact accagagcgg cctgtccatc | 660 |
| gtgatgcctg tgggcggcca gagcagcttc tacagcgact ggtacagccc cgcctgtggc | 720 |
| aaagccggct gccagaccta caagtgggag acattcctga cctccgagct gccccagtgg | 780 |
| ctgagcgcca atagagccgt gaagcctaca ggctctgccg ccatcggact gagcatggcc | 840 |
| ggaagctctg ccatgatcct ggccgcctat caccctcagc agttcatcta cgccggcagc | 900 |
| ctgtctgccc tgctggaccc ttctcagggc atgggcccct tctctgatcg actggctatg | 960 |
| ggcgacgctg gcggatacaa ggccgccgat atgtggggcc ctagcagcga tcctgcctgg | 1020 |
| gagagaaacg accccaccca gcagatcccc aagctggtgg ccaacaacac ccggctgtgg | 1080 |
| gtgtactgcg gcaacggcac ccctaatgaa ctgggcggag ccaatatccc cgccgagttc | 1140 |
| ctggaaaact tcgtgcggag cagcaacctg aagttccagg atgcctacaa cgccgctggc | 1200 |
| ggccacaacg ccgtgttcaa cttccctccc aatggcaccc acagctggga gtactgggga | 1260 |
| gcccagctga acgccatgaa gggcgatctg cagtcctctc tgggagccgg ctaatttttc | 1320 |
| t | 1321 |

<210> SEQ ID NO 18
<211> LENGTH: 718
<212> TYPE: DNA
<213> ORGANISM: artificial sequence
<220> FEATURE:
<223> OTHER INFORMATION: nt sequence coding for the fusion of Rv3407 and Rv1813** Mtb antigens with peptide 2A in between

<400> SEQUENCE: 18

```
accatgagag ccaccgtggg actggtggaa gccatcggca tcagagagct gagacagcac    60
gccagcagat acctggccag agtggaagcc ggcgaggaac tgggcgtgac caacaagggc   120
agactggtgg ccagactgat ccctgtgcag gccgccgaga aagcagaga ggccctgatt   180
gagagcggcg tgctgatccc tgccagacgg cctcagaacc tgctggatgt gacagccgag   240
cccgccagag gccggaagag aaccctgagc gacgtgctga acgagatgcg ggatgaacag   300
gggtcaggac agtgcaccaa ctacgctctc ctgaaactgg ccggcgatgt ggaaagcaac   360
cctggccctg atgcccatct ggccaacggc agcatgagcg aagtgatgat gagcgagatc   420
gccggcctgc ccatccctcc catcatccac tatggcgcca ttgcctacgc ccctagcggc   480
gcctctggaa aagcttggca tcagagaaca cccgccagag ccgaacaggt ggccctggaa   540
aagtgcggcg acaagacctg caaggtggtg tcccggttca ccagatgtgg cgccgtggcc   600
tacaacggct ccaagtatca gggcggcacc ggcctgacaa aagggccgc tgaggacgac   660
gccgtgaaca ggctggaggg aggcagaatc gtgaactggg cctgcaacta attttttct   718
```

<210> SEQ ID NO 19
<211> LENGTH: 649
<212> TYPE: DNA
<213> ORGANISM: artificial sequence
<220> FEATURE:
<223> OTHER INFORMATION: nt sequence coding fro the fusion of Rv3407 and
      Rv1813* Mtb antigens

<400> SEQUENCE: 19

```
accatgagag ccaccgtggg actggtggaa gccatcggca tcagagagct gagacagcac    60
gccagcagat acctggccag agtggaagcc ggcgaggaac tgggcgtgac caacaagggc   120
agactggtgg ccagactgat ccctgtgcag gccgccgaga aagcagaga ggccctgatt   180
gagagcggcg tgctgatccc tgccagacgg cctcagaacc tgctggatgt gacagccgag   240
cccgccagag gccggaagag aaccctgagc gacgtgctga acgagatgcg ggatgaacag   300
gatgcccatc tggccaacgg cagcatgagc gaagtgatga tgagcgagat cgccggcctg   360
cccatccctc ccatcatcca ctatggcgcc attgcctacg ccctagcgg cgcctctgga   420
aaagcttggc atcagagaac acccgccaga gccgaacagg tggccctgga aaagtgcggc   480
gacaagacct gcaaggtggt gtcccggttc accagatgtg cgccgtggc ctacaacggc   540
tccaagtatc agggcggcac cggcctgaca agaaggccg ctgaggacga cgccgtgaac   600
aggctggagg gaggcagaat cgtgaactgg gcctgcaact aattttttct             649
```

<210> SEQ ID NO 20
<211> LENGTH: 100
<212> TYPE: DNA
<213> ORGANISM: Vaccinia virus

<400> SEQUENCE: 20

```
tatattatta agtgtggtgt ttggtcgatg taaaattttt gtcgataaaa attaaaaaat    60
aacttaattt attattgatc tcgtgtgtac aaccgaaatc                        100
```

<210> SEQ ID NO 21
<211> LENGTH: 114
<212> TYPE: DNA
<213> ORGANISM: Vaccinia virus

<400> SEQUENCE: 21
tttattctat acttaaaaaa tgaaaataaa tacaaaggtt cttgagggtt gtgttaaatt    60
gaaagcgaga aataatcata aattatttca ttatcgcgat atccgttaag tttg          114

<210> SEQ ID NO 22
<211> LENGTH: 40
<212> TYPE: DNA
<213> ORGANISM: artificial sequence
<220> FEATURE:
<223> OTHER INFORMATION: early late promoter of vaccinia virus

<400> SEQUENCE: 22
aaaaattgaa attttatttt ttttttttgg aatataaata                          40

<210> SEQ ID NO 23
<211> LENGTH: 124
<212> TYPE: DNA
<213> ORGANISM: Vaccinia virus

<400> SEQUENCE: 23
ccacccactt tttatagtaa gttttcacc cataaataat aaatacaata attaatttct     60
cgtaaaagta gaaatatat tctaatttat tgcacggtaa ggaagtagaa tcataaagaa    120
cagt                                                                124

<210> SEQ ID NO 24
<211> LENGTH: 50
<212> TYPE: DNA
<213> ORGANISM: Vaccinia virus

<400> SEQUENCE: 24
caagtgacaa caaaaaatga attaataata agtcgttaac gtacgccgcc               50

<210> SEQ ID NO 25
<211> LENGTH: 298
<212> TYPE: DNA
<213> ORGANISM: Mycobacterium tuberculosis

<400> SEQUENCE: 25
accatgaccg agcagcagtg gaacttcgcc ggaattgagg ccgctgccag cgccatccag    60
ggcaacgtga catccatcca cagcctgctg gacgagggca agcagagcct gacaaaactg   120
gctgctgcct ggggcggctc tggctctgaa gcttatcagg gcgtgcagca gaagtgggac   180
gccaccgcca ccgagctgaa caacgccctg cagaacctgg cccggacaat ctctgaagcc   240
ggacaggcca tggccagcac cgagggcaat gtgaccggca tgtttgcctg atttttct    298

<210> SEQ ID NO 26
<211> LENGTH: 313
<212> TYPE: DNA
<213> ORGANISM: Mycobacterium tuberculosis

<400> SEQUENCE: 26
accatggccg agatgaagac cgatgccgcc accctggctc aggaagccgg caacttcgag    60
agaatcagcg gcgacctgaa aacccagatc gaccaggtgg aaagcaccgc cggatctctg   120
cagggacagt ggcgggagc tgctggaaca gctgctcagg ctgctgtcgt gcggtttcag   180
gaagctgcca acaagcagaa gcaggaactg gacgagatca gcaccaacat ccggcaggcc   240
ggcgtgcagt acagcagagc cgatgaggaa cagcagcagg ccctgtccag ccagatgggc   300
ttttgatttt tgt                                                      313

<210> SEQ ID NO 27
<211> LENGTH: 442
<212> TYPE: DNA
<213> ORGANISM: Mycobacterium tuberculosis

<400> SEQUENCE: 27
accatgacaa ccgccagaga catcatgaac gccggcgtga cctgtgtggg cgagcacgag 60
acactgacag ccgccgctca gtacatgaga gagcacgaca tcggcgccct gcccatctgc 120
ggcgacgatg atagactgca cggcatgctg accgaccggg acatcgtgat caagggcctg 180
gctgctggcc tggaccccaa tactgctaca gctggcgagc tggcaagaga cagcatctac 240
tacgtggacg ccaacgccag catccaggaa atgctgaacg tgatggaaga acaccaggtc 300
cgacgggtgc ccgtgatcag cgaacacaga ctcgtgggca tcgtgaccga ggccgatatc 360
gccagacatc tgcccgagca cgccatcgtg cagttcgtga aggccatctg cagccccatg 420
gccctggcct cttgattttt ct 442

<210> SEQ ID NO 28
<211> LENGTH: 874
<212> TYPE: DNA
<213> ORGANISM: artificial sequence
<220> FEATURE:
<223> OTHER INFORMATION: nt sequence coding for mutant Ag85B* Mtb antigen

<400> SEQUENCE: 28
accatggcct tctctagacc tggcctgccc gtggaatacc tgcaggtccc aagccccagc 60
atgggccggg atatcaaggt gcagtttcag agcggcggca acaacagccc tgccgtgtat 120
ctgctggatg gcctgagagc ccaggacgac tacaacggct gggacatcaa cacccctgcc 180
ttcgagtggt actaccagag cggcctgtcc atcgtgatgc ctgtgggcgg ccagagcagc 240
ttctacagcg actggtacag ccccgcctgt ggcaaagccg gctgccagac ctacaagtgg 300
gagacattcc tgacctccga gctgccccag tggctgagcg ccaatagagc cgtgaagcct 360
acaggctctg ccgccatcgg actgagcatg gccggaagct ctgccatgat cctggccgcc 420
tatcaccctc agcagttcat ctacgccggc agcctgtctg ccctgctgga cccttctcag 480
ggcatgggcc cttctctgat cggactggct atgggcgacg ctggcggata caaggccgcc 540
gatatgtggg gccctagcag cgatcctgcc tgggagagaa acgaccccac ccagcagatc 600
cccaagctgg tggccaacaa cacccggctg tgggtgtact gcggcaacgg cacccctaat 660
gaactgggcg gagccaatat ccccgccgag ttcctggaaa acttcgtgcg gagcagcaac 720
ctgaagttcc aggatgccta caacgccgct ggcggccaca acgccgtgtt caacttccct 780
cccaatggca cccacagctg ggagtactgg ggagcccagc tgaacgccat gaagggcgat 840
ctgcagtcct ctctgggagc cggctgattt ttgt 874

<210> SEQ ID NO 29
<211> LENGTH: 304
<212> TYPE: DNA
<213> ORGANISM: Mycobacterium tuberculosis

<400> SEQUENCE: 29
accatgagcc tgctggacgc ccacatccct cagctggtgg ccagccagtc tgcctttgcc 60
gccaaagccg gcctgatgag acacaccatt ggccaggccg aacaggccgc catgtctgcc 120
caggcttttc accagggcga aagcagcgcc gcctttcagg ccgcccatgc cagatttgtg 180

```
gccgctgccg ctaaagtgaa caccctgctg gatgtggccc aggccaatct gggagaagcc      240
gccggaactt acgtggccgc agatgccgct gctgccagca cctacacagg cttctgattt      300
ttct                                                                  304
```

<210> SEQ ID NO 30
<211> LENGTH: 301
<212> TYPE: DNA
<213> ORGANISM: Mycobacterium tuberculosis

<400> SEQUENCE: 30

```
accatgagcc agatcatgta caactacccc gccatgctgg ccacgccgg cgatatggct       60 ggatatgccg gcacactgca gagcctgggt gccgagattg ccgtggaaca ggctgccctc     120
cagtctgcct ggcagggcga taccggcatc acataccagg cttggcaggc ccagtggaac     180
caggccatgg aagatctcgt gcgggcctac cacgccatga gcagcacaca cgaggccaac     240
accatggcca tgatggcccg ggatacagcc gaggccgcta agtggggagg ataatttttc     300
t                                                                     301
```

<210> SEQ ID NO 31
<211> LENGTH: 310
<212> TYPE: DNA
<213> ORGANISM: Mycobacterium tuberculosis

<400> SEQUENCE: 31

```
accatgagag ccaccgtggg actggtggaa gccatcggca tcagagagct gagacagcac       60
gccagcagat acctggccag agtggaagcc ggcgaggaac tgggcgtgac caacaagggc     120
agactggtgg ccagactgat ccctgtgcag gccgccgaga aagcagaga ggccctgatt      180 gagagcggcg tgctgatccc tgccagacgg cctcagaacc tgctggatgt gacagccgag     240
cccgccagag gccggaagag aaccctgagc gacgtgctga cgagatgcg ggatgaacag      300 taattttct                                                             310
```

<210> SEQ ID NO 32
<211> LENGTH: 1192
<212> TYPE: DNA
<213> ORGANISM: Mycobacterium tuberculosis

<400> SEQUENCE: 32

```
accatggtgg acttcggcgc cctgcctccc gagattaata cgccaggat gtacgccggc        60 cctggcagcg cttctctggt ggccgctgcc aagatgtggg atagcgtggc cagcgacctg     120
ttctctgccg ccagcgcatt tcagagcgtc gtgtggggac tcactgtggg ctcttggatc     180
ggatcttctg ccggtctgat ggccgctgct gcctctcctt atgtggcctg gatgagcgtg     240
accgccggac aggcacagct gacagctgca caggtccgag tggctgccgc cgcttacgag     300
acagcctaca gactgacagt gcctccaccc gtgatcgccg agaatcggac cgagctcatg     360
accctgaccg ccaccaatct gctcggccag aacacccctg ccatcgaggc caatcaggcc     420
gcctactctc aaatgtgggg ccaagatgcc gaggctatgt acggctatgc agccacagcc     480
gccactgcta cagaagccct gctgcccttc gaagatgccc tctgatcac aaaccctggc     540 ggcctgctgg aacaggccgt ggctgtggaa gaggccatcg ataccgctgc cgccaaccaa     600
ctcatgaaca acgtgccaca ggccctccag cagctggctc agcctgctca gggcgtggtg     660
ccttctagca agctcggcgg actgtggacc gccgtgtctc ctcatctgag ccctctgagc     720
```

```
aacgtgtcct ctatcgccaa caaccacatg agcatgatgg gcaccggcgt gtccatgacc    780
aacaccctgc acagcatgct gaagggactg gcccctgctg ctgcccaggc tgtggaaaca    840
gccgccgaaa atggcgtgtg ggccatgagc agcctgggct ctcagctggg aagctccctc    900
ggttcttctg gactgggagc tggcgtggcc gccaatctgg gaagagctgc ttctgtcggc    960
agcctgtctg tgcctcctgc ttgggccgct gctaaccagg ctgtgacacc agctgctaga   1020
gccctgcctc tgaccagcct gacatctgcc gctcagacag cccctggcca catgctggga   1080
ggactgcctc tgggccactc tgtgaatgcc ggcagcggca tcaacaacgc cctgagagtg   1140
cctgccagag cctacgccat ccccagaact ccagccgctg gctaattttt gt           1192

<210> SEQ ID NO 33
<211> LENGTH: 307
<212> TYPE: DNA
<213> ORGANISM: Mycobacterium tuberculosis

<400> SEQUENCE: 33
accatgagct tcaccgccca gcctgaaatg ctggccgctg ctgctggcga gctgagatct     60
ctgggagcca cactgaaggc cagcaatgcc gctgccgccg tgcctacaac aggcgtggtg    120
cctcctgccg ccgatgaagt gtctctgctg ctggccaccc agttcagaac ccacgccgcc    180
acataccaga ccgcctctgc caaagccgcc gtgatccacg agcagttcgt gaccacactg    240
gccaccagcg ccagctccta cgccgataca gaggccgcca atgccgtcgt gacaggctga    300
tttttct                                                              307
```

FUSION OF HETEROOLIGOMERIC MYCOBACTERIAL ANTIGENS

This invention was made with government support under grant number 1R01-AI098911 awarded by the National Institute of Allergy and Infectious Diseases. The Government therefore has certain rights in the invention.

CROSS REFERENCE TO RELATED APPLICATIONS

This application is a national phase application based on PCT/EP2015/050344, filed Jan. 9, 2015, which claims the priority of French Patent Application No. 14305030.0, filed Jan. 9, 2014, the contents of both of which are incorporated herein by reference.

FIELD OF THE INVENTION

The present invention relates generally to novel immunogenic combinations comprising or encoding at least two heterooligomeric mycobacterial antigens or a nucleic acid molecule encoding such heterooligomeric mycobacterial antigens, where the mycobacterial antigens are selected from the group of Esx, PE and PPE antigens of a *Mycobacterium* species, particularly a *Mycobacterium* of the tuberculosis complex such as *Mycobacterium tuberculosis* (Mtb). In a preferred embodiment, the immunogenic combination is in the form of a fusion polypeptide comprising at least the two heterooligomeric mycobacterial antigens. The present invention also relates to vectors, host cells and compositions comprising or encoding said immunogenic combination as well as to methods for expressing and producing it. The present invention also relates to methods of using said immunogenic combination, fusion polypeptide, vector, host cell, composition particularly for inducing or stimulating an immune response with the goal of providing a protective response against a *Mycobacterium* infection or any disease caused by or associated with a *Mycobacterium* infection.

BACKGROUND OF THE INVENTION

With an estimated one third of the world's population infected with *Mycobacterium tuberculosis* (Mtb) (i.e. more than two billion individuals) and 9 to 10 million new cases and 2 million deaths every year, tuberculosis (TB) is a global and worldwide health problem. Generally, person-to-person transmission occurs by aerosolized droplets generated by a person suffering from pulmonary TB (active disease). Among those infected (an estimated 30% of exposed individuals), only 5-10% will develop active TB disease within 2 years post-exposure (known as primary TB). However, the majority of infected individuals develop latent infection (LTBI) which can last decades without clinical signs or symptoms of disease. LTBI represents a state of equilibrium in which the infected subject is able to control the infection but not completely eradicate the bacteria. Reactivation (active TB after remote infection) may occur at a later stage, particularly in the elderly or in immunocompromised individuals as in the case of HIV infection and treatment with TNF inhibitors. The risk of TB reactivation is estimated as 10% per lifetime and impaired immunity increases the risk to 10% per year.

*Mycobacterium tuberculosis* (Mtb) *bacillus*, the causative agent of TB, possesses a circular genome of 4 411 529 base pairs (bp) which was fully sequenced in 1998 (Cole et al., 1998, Nature 393: 537-44). Mtb encodes approximately 4000 genes; however the function and role in Mtb life cycle and pathogenesis of the majority of these genes have not yet been elucidated.

Analysis of the genome sequences from closely related mycobacteria and comparative studies have permitted to identify a number of secreted proteins, including members of the Esx and PE/PPE gene families.

Although no structure or precise function is known for the various members of the PE/PPE families, it has been suggested that some of them may play a role in immune evasion, virulence and host specificity of the infecting *Mycobacterium*. Genome analyses revealed that the PE and PPE genes are frequently found adjacent in the Mtb genome and functionally linked (Riley et al., 2008, PLoS Comput Biol, 4:e1000174). It is thus assumed that such pairs of PE/PPE proteins (e.g. Rv2431c/Rv2430, Rv3477/Rv3478, etc) are interacting each other to form heterodimers which are likely the functional forms of these proteins.

As the PE and PPE gene family, the majority of Esx genes are expressed as tandem pairs that are coordinately regulated. The *M. tuberculosis* genome contains 23 EsX genes (named Esx A to W), which encode proteins presumably linked to Mtb virulence. Biophysical studies indicate that gene products of Esx pairs interact each other in functional heterodimers. For illustrative purpose, structural analysis of the TB9.8 (Rv0287)/TB10.4 (Rv0288) complex revealed that 19 amino acid residues from TB9.8 and 21 amino acid residues from TB10.4 are involved in the intramolecular contacts (Ilghari et al., 2011, J. Biol. Chem., 286: 29993-30002).

Previous attempts to overexpress Mtb EsxA (ESAT6) and EsxB (CFP 10) proteins of *M. tuberculosis* individually in *E. coli* were hampered by technical difficulties which resulted in low yields of protein. Several studies tend to indicate that expression of related protein pairs together would facilitate appropriate folding and dimerization permitting high yields of recombinant protein to be produced which simplify structural and biochemical studies of these protein families involved in Mtb virulence (Strong et al., 2006, Proc. Natl. Acad. Sci, 103: 8060-5; Mehra et al., 2013, PLoS, 9: e1003734). However, there is no indication that such dimers retain immunogenic activities.

Mtb-caused million deaths every year are particularly dramatic considering that both vaccine (Bacille-Calmette-Guérin (BCG)) and antibiotics exist and are widely used. However, if BCG appears to be effective at preventing disease in newborns and toddlers, it does not protect adults and fails to prevent Mtb reactivation in latently infected persons. On the other hand, treatment of active TB with various antibiotic combinations appears efficacious but requires strong patient compliance with daily administrations of different drugs over several months. Moreover, there is an alarming rate of appearance of drug resistant Mtb strains (e.g. "MultiDrug Resistant" (MDR), "eXtensively Drug-Resistant" (XDR) and "Totally Drug Resistant" (TDR) strains), mostly because of improper observance of this lengthy and costly drug regimen treatment.

There are several lines of evidence suggesting that stimulation of the cellular immune system plays a role in controlling TB disease (Rook et al., 2007, J Infect Dis, 196: 191-8). The central role of CD4 T lymphocytes to control the pathogen and to prevent progression to disease is well established. For instance, HIV/AIDS patients with low $CD4^+$ T cells count are more susceptible to progression to TB disease while antiviral treatments that elevate $CD4^+$ T cells reduce progression to TB disease. However, CD4 T cells do not operate alone and are supported by CD8 T cells and other T cell subsets.

Development of effective TB vaccines is therefore a priority in this worrying context and two main approaches are being investigated for the last decade: replacement of BCG and BCG booster.

BCG replacement candidates aim at improving BCG efficacy and safety and are mainly based on live attenuated bacteria such as genetically modified BCG or Mtb strains engineered to express new sets of antigens that are absent from BCG or to overexpress Mtb antigens that BCG expresses but at a likely insufficient level or still to delete virulence genes and their regulators (e.g WO2009/064825; WO2012031752).

BCG boosters aim at inducing cellular and/or humoral immune responses and generally rely on recombinant vaccines designed for providing various TB antigens, either as protein composition generally admixed with potent Th1-activating adjuvants or through viral expressing vectors (see Andersen, 2007, Nature, 5: 484; Ottenhoff and Kaufman, 2012, PLoS 8(5): e1002607; Cayabyab et al., 2012, Frontiers in Cellular and Infection Microbiology 2: 1-16; and Brennan et al., 2012, Int J Tuberc. Lung Dis. 16(12): 1566-1573).

Some of these vaccine candidates have produced results in preclinical and clinical studies that demonstrate an ability to induce a robust cellular mediated immune response against Mtb or to provide protection against TB-associated lung lesions. For example, an adenoviral vector expressing Ag85A, TB10.4, TB9.8 and Acr2 (AdTBF) improved the effects of BCG, reducing lesion volume and bacterial load in the lungs of vaccinated goats (Perez de Val et al., 2013, PLoS, 8: e81317). However, these studies have highlighted the influence of various factors on the T cell response and protective efficacy such as the antigen doses (e.g. Aagaard et al., 2009, PLoS One, 4: 1-8) and administration routes (Goonetilleke et al., 2003, J. Immunol., 171: 1602-9).

The use of fusion polypeptides comprising various TB antigens has also been described. For example, the fusion protein Hyvac 4 (H4), which consists of Ag85B fused to TB10.4 (Aagaard et al., 2009, PLoS One, 4: 1-8) is in clinical development. The GSK's M72 fusion protein made of Rv1196 inserted in the middle of the serine protease Rv0125 showed a favorable clinical profile in terms of safety and immunogenicity when administered with different synthetic adjuvants (Von Eschen et al., 2009, Hum Vaccine, 5: 475-82). One may also cite the so-called "ID" fusion proteins (WO2008/124647) such as ID83 made of Rv1813, Rv3620 and Rv2608 and ID93 including Rv3619 fused to the three ID83 antigens as well as fusions of Rv0198 antigen with either Rv3812 or Rv0111 (see WO2011/144951). On the other hand, WO2014/009438 describes large fusions involving numerous mycobacterial antigens representative of all phases of the natural course of infection.

Despite all these and other efforts, tuberculosis is far from being controlled and there remains a need for alternative vaccine candidates for diagnosing, preventing and treating tuberculosis, especially in endemic regions.

The present invention fulfils this and other needs by providing an immunogenic combination which comprises at least heterooligomeric mycobacterial antigens preferably in fusion, which are selected from the group of the Esx, PE and PPE antigens. The combination/fusion of pairs of mycobacterial antigens involved in such heterooligomers (e.g. heterodimers) offers unexpected properties such as improvement of the antigen folding and the solubility of the fused antigens as compared to the individual antigens, which may increase genetic stability of the vaccine candidate, decrease potential cytotoxicity when produced in host cell or organism and/or improve quality and/or scope of the anti-*Mycobacterium* immunogenic response, whether humoral and/or cellular. In addition, the immunogenic combination of the invention may be tailored for different phases of the natural course of *Mycobacterium* infection with additional mycobacterial antigens. The present invention is particularly useful in the context of immunotherapy as stand-alone or as BCG booster for preventive or therapeutic purposes in the *Mycobacterium* infection field, e.g. preventing Mtb infection and/or prevention of primary TB and/or prevention of reactivation in latently infected subjects. It can also be used in association with standard (e.g. antibiotic-therapy) or any other novel treatment that is currently developed (e.g. small direct or indirect inhibitor molecules; antibodies or immunotherapeutics, etc). The present invention would also be helpful in the veterinary field, for example to reduce or abolish the risk of *Mycobacterium* infection and/or active disease in animals, especially in bovine and goat breedings.

This technical problem is solved by the provision of the embodiments as defined in the claims.

Other and further aspects, features and advantages of the present invention will be apparent from the following description of the presently preferred embodiments of the invention. These embodiments are given for the purpose of disclosure.

DETAILED DESCRIPTION OF THE INVENTION

The present invention relates to an immunogenic combination comprising or encoding at least two heterooligomeric mycobacterial antigens preferably a fusion polypeptide thereof, which are selected from the group of the Esx, PE and PPE antigens or a nucleic acid molecule encoding said combination/fusion.

Definitions

As used herein throughout the entire application, the terms "a" and "an" are used in the sense that they mean "at least one", "at least a first", "one or more" or "a plurality" of the referenced compounds or steps, unless the context dictates otherwise.

The term "and/or" wherever used herein includes the meaning of "and", "or" and "all or any other combination of the elements connected by said term".

The term "about" or "approximately" as used herein means within 10%, preferably within 8%, and more preferably within 5% of a given value or range.

The terms "amino acids", "residues" and "amino acid residues" are synonyms and encompass natural amino acids as well as amino acid analogs (e.g. non-natural, synthetic and modified amino acids, including D or L optical isomers).

As used herein, when used to define products, compositions and methods, the term "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are open-ended and do not exclude additional, unrecited elements or method steps. Thus, a polypeptide "comprises" an amino acid sequence when the amino acid sequence might be part of the final amino acid sequence of the polypeptide. Such a polypeptide can have up to several hundred additional amino acids residues (e.g. linker and targeting peptides as described herein). "Consisting essentially of" means excluding other components or steps of any essential significance. Thus, a composition consisting essentially of the recited components would not exclude trace contaminants and pharmaceutically acceptable carriers. A polypeptide "consists essentially of" an amino acid sequence when such an amino acid sequence is present with eventually only a few additional amino acid residues. "Consisting of" means excluding more than trace elements of other components or steps. For example, a polypeptide "consists of" an amino acid sequence when the polypeptide does not contain any amino acids but the recited amino acid sequence.

The term "polypeptide" as used herein refers to a polymer of amino acids residues of at least eight or more amino acids bonded via covalent peptide bonds. The polypeptide can be linear or branched and may comprise naturally occurring and/or amino acid analogs. The term also encompasses an amino acid polymer that has been modified naturally or by intervention; for example, disulfide bond formation, glycosylation, lipidation, acetylation, phosphorylation, or any other manipulation or modification, such as conjugation with a labeling component or addition of functional peptides such as tag (his, myc, Flag, etc) targeting peptide (signal peptide, trans-membrane domain, etc), as well as other modifications known in the art. It will be understood that the term "polypeptide" encompasses proteins (usually employed for polypeptides comprising 50 or more amino acid residues), oligopeptides, and peptides (usually employed for polypeptides comprising less than 50 amino acid residues). Each polypeptide may thus be characterized by specific amino acids and be encoded by specific nucleic acid sequences.

The term "combination" as used herein refers to any arrangement possible of various components. Such an arrangement includes mixture of mycobacterial antigens (e.g. mixture of individual antigens and/or fusion of antigens) or mixture of nucleic acid molecules (e.g. carried by one or more vector) as well as mixture of polypeptide(s) and nucleic acid molecule(s). The present invention encompasses combinations comprising equal molar concentrations of each component as well as combinations with very different concentrations. It is appreciated that optimal concentration of each *Mycobacterium* component can be determined by the artisan skilled in the art.

The term "immunogenic" refers to the ability to induce or stimulate a measurable cellular and/or humoral immune response in a subject into which the component qualified as immunogenic has been introduced. For example, the combination of the invention is immunogenic in the sense as it is capable of inducing or stimulating an immune response in a subject which can be innate and/or specific (i.e. against at least one mycobacterial antigen/epitope comprised in or expressed by said immunogenic combination), humoral and/or cellular (e.g. production of antibodies and/or cytokines and/or the activation of cytotoxic T cells, B cells, T lymphocytes, antigen presenting cells, helper T cells, dendritic cells, NK cells, etc) and usually results in a protective response in the administered subject. A vast variety of direct or indirect biological assays are available in the art to evaluate the immunogenic nature of a component either in vivo (animal or human being), or in vitro (e.g. in a biological sample) as described herein. For example, the ability of a particular antigen to stimulate a cell-mediated immunological response may be determined by a number of assays, such as by lymphoproliferation (lymphocyte activation) assays, CTL cytotoxic cell assays, or by assaying for T lymphocytes specific for the antigen in a sensitized subject.

The term "fusion" or "fusion polypeptide" as used herein refers to the covalent linkage in a single polypeptide chain of two or more polypeptides and is performed by genetic means, i.e. by fusing in frame the nucleic acid molecules encoding each of said polypeptides. By "fused in frame", it is meant that the expression of the fused coding sequences results in a single polypeptide without any translational terminator between each of the fused polypeptides. The fusion can be direct (i.e. without any additional amino acid residues in between) or indirect (e.g. through a linker between the fused polypeptides) and can take place at the N or C terminus of a polypeptide or internally. The presence of a linker may facilitate correct folding and/or functioning of the fused polypeptides. The linker may also include a cleavage site with the goal of cleaving the fused polypeptides during (e.g 2a peptide) or after translation (e.g a protease site) in the host cell or organism. The present invention is not limited by the form, size or number of linker sequences employed. For illustrative purposes, typical linkers are 3 to 30 amino acids long and composed of repeats of amino acid residues such as glycine, serine, threonine, asparagine, alanine and/or proline. The linker can also be a peptide sequence from a prokaryote organism (e.g. a *Mycobacterium* such as Mtb) that is particularly flexible or that is already present in the N-terminal portion of some antigens (such a signal peptide).

As used herein, the term "mycobacterial antigen" refers to a polypeptide present in (e.g. encoded by the genome of a *Mycobacterium* species) or obtained from a *Mycobacterium* species. In the context of the invention, this term encompasses native mycobacterial polypeptide as well as fragment and modified version thereof (i.e. variant) as described hereinafter. Preferably, the mycobacterial antigen(s) in use in the present invention is/are immunogenic upon introduction in the subject (capable of being bound by an antibody or a T cell receptor). Typically, it contains one or more B and/or T epitope(s), in particular CTL or $T_H$ epitope(s) or both, involved in recognition by a particular antibody or T-cell receptor in the context of the Major Histocompatibility Complex (MHC). Methods to identify such epitopes are well known in the art. For example, T cell epitopes can be identified by implementing biological assays (e.g. IFNγ assays using libraries of synthetic overlapping oligopeptides) or available prediction programs.

A "native" mycobacterial antigen can be found, isolated, obtained from a source of *Mycobacterium* in nature. Such sources include biological samples (e.g. blood, plasma, sera, saliva, sputum, tissue sections, biopsy specimen etc.) collected from a subject infected or that has been exposed to a *Mycobacterium*, cultured cells as well as recombinant materials available in depositary institutions (e.g. ATCC or TB institutions), libraries or described in the literature (e.g. *Mycobacterium* isolates, *Mycobacterium* genomes, genomic fragments, genomic RNA or cDNA as well as any plasmid and vector known in the art to include such elements).

A "fragment" of a mycobacterial antigen is a polypeptide comprising at least 8 contiguous amino acids of a mycobacterial antigen, more preferably at least 15 contiguous amino acids, more preferably at least about 20 contiguous amino acids, even more preferably at least about 25 contiguous amino acids, even more preferably at least about 30 contiguous amino acids, even more preferably at least about 40 contiguous amino acids. Such a fragment may be characterized as retaining a capacity of stimulating an immune response as the mycobacterial antigen. A suitable fragment can be an immunogenic domain (usually of 8-30 amino acid residues) comprising one or more peptide motif(s) recognized by an antibody, a T-cell receptor or a HLA molecule.

A "modified", "variant" or "mutant" mycobacterial antigen typically differs from a polypeptide specifically disclosed herein or a native one in one or more position(s). Any modification(s) can be envisaged, including substitution, insertion, addition and/or deletion of one or more amino acid residue(s), non-natural arrangements and any combination of these possibilities. Amino acid substitution can be conservative or not. When several modifications are contemplated, they can concern consecutive residues and/or non-consecutive residues. Such modification(s) can be beneficial to the synthesis, processing, stability, function and/or solubility of the resulting variant polypeptide and/or to its immunogenicity. Modification(s) can be generated by a number of ways known to those skilled in the art, such as site-directed mutagenesis (e.g. using the Sculptor™ in vitro mutagenesis system of Amersham, Les Ullis, France), PCR mutagenesis, DNA shuffling and by synthetic techniques (e.g. resulting in a synthetic nucleic acid molecule encoding the desired polypeptide variant).

The term "heterooligomeric" as used herein refers to the ability of two components to form a complex. The association can be specific (requiring a structural complementarity between amino acid residues of the two partners at a binding site and one or more type(s) of electrostatic forces, hydrogen bonding, hydrophobic forces, and/or van der Waals forces to maintain the binding) or non-specific (interaction through one or more type(s) of the above-cited forces but lacking the structural complementarily). A number of mycobacterial antigens of the Esx, PE or PPE gene family are prone to associate and form a complex (heterooligomer) in the natural context (e.g. a *Mycobacterium* infection), such as 1:1 complex (heterodimer) or any other types of association between the two partners (e.g. trimer, tetramer, etc). The formation of such a heterooligomer can be easily demonstrated by circular dichroism or by Western blotting or through labeling techniques. Alternatively, it can also be determined by conventional structural techniques such as X-ray crystallography, NMR or SHG.

As used herein, the terms "*Mycobacterium*", "*Mycobacterium* species" and "mycobacterial" are used interchangeably to refer to any member of the genus of *Actinobacteria* belonging to the Mycobacteriaceae family. The terms encompass laboratory strains as well as clinical isolates.

A "*Mycobacterium* infection" refers to the exposure of a subject to a *Mycobacterium* species followed by a colonization of the subject or the subject's tissue(s) by the bacterium. The colonization can cause serious diseases (e.g. tuberculosis, leprosy, Bureli ulcer etc, depending on the *Mycobacterium*), or can result in no adverse signs (asymptomatic or latent infection).

The term "treating" (and any form of treating such as "treatment", "treat") as used herein encompasses prophylaxis (e.g. prevention of a subject at risk of being infected with a *Mycobacterium*) and/or therapy (e.g. a subject diagnosed as being infected with a *Mycobacterium*). Treatment requires administer externally or internally to a subject an active agent (e.g. the immunogenic combination, fusion polypeptide, nucleic acid molecule, vector and/or composition described herein), eventually in association with conventional therapeutic modalities, especially the one currently used in the treatment of active *Mycobacterium* disease (e.g. TB).

The term "subject" generally refers to a vertebrate that would benefit from induction or stimulation of an immune response against a *Mycobacterium* species and particularly a mammalian selected from the group consisting of domestic animals, farm animals, sport animals, and primates. Preferably, the subject is a human who has been diagnosed as being or at risk of being infected with a *Mycobacterium* and especially Mtb and thus is susceptible of having or at risk of having a disease or condition caused by or associated with a *Mycobacterium* infection (e.g. active or latent tuberculosis).

The term "isolated" when used to describe a polypeptide, nucleic acid molecule, vector, etc disclosed herein means that such polypeptide, nucleic acid molecule, vector, etc is removed from its natural environment (i.e. separated from at least one other component(s) with which it is naturally associated). For illustrative purpose, an isolated polypeptide encompasses a recombinant polypeptide usually produced within a recombinant cell engineered to express it, since at least one component of the polypeptide's natural environment will not be present. Ordinarily, however, an isolated polypeptide will be prepared by at least one purification step.

The term "obtained from", "originating" or "originate" is used to identify the original source of a component (e.g. polypeptide, nucleic acid molecule, vector, etc) but is not meant to limit the method by which the component is made which can be, for example, by chemical synthesis or recombinant means.

*Mycobacterium* Species

As defined above, the mycobacterial antigens (such as the heterooligomeric mycobacterial antigens and optionally the one or more additional mycobacterial antigen(s) comprised or encoded by the immunogenic combination of the invention) can independently be obtained from any member of a *Mycobacterium* (*M.*) species identified at present time.

A vast number of Mycobacteria for use in the context of the invention are described in the art. Exemplary *Mycobacterium* species include without limitation *M. phlei, M. smegmatis, M. africanum, M. canetti, M. fortuitum, M. marinum, M. ulcerans, M. tuberculosis* (Mtb), *M. paratuberculosis, M. bovis, M. microti, M. celatum M. avium, M. leprae, M. lepraemurium, M. intracellulare, M. scrofulaceum, M. xenopi, M. genavense, M. kansasii, M. simiae, M. szulgai, M. haemophilum, M. asiaticum, M. malmoense, M. vaccae, M. caprae, M. pinnipedii* and *M. shimoidei*.

In a preferred embodiment, the mycobacterial antigens in use in this invention are obtained from a *Mycobacterium* species of the tuberculosis complex which includes those species traditionally considered as causing the disease tuberculosis, as well as *Mycobacterium* environmental and opportunistic species that cause tuberculosis and pulmonary disease in immune compromised subjects (e.g. HIV-infected patients). Exemplary species of the tuberculosis complex for use herein include without limitation *M. tuberculosis* (Mtb), *M. bovis, M. bovis* BCG, *M. africanum, M. canetti, M. caprae*, and *M. microti*. A preferred embodiment is directed to Mtb including the Mtb laboratory strains such as H37Rv and H37Ra and clinical isolates such as KZN4207, T85, CDC1551 (isolated in the US), F11 (isolated in South Africa), C, K85 (isolated in Netherland), CPHL-A, as well as the MDR or XDR isolates such as TN5904, Haarlem, KZN1435, Bejing and KZN605. Other preferred species for mycobacterial antigen sources are *M. bovis, M. bovis* BCG and *M. caprae*, especially for veterinary use. However, one would indeed expect cross-reactivity given the high percentage of homology existing between the *M.* species at the amino acid and nucleotide levels. Thus, the immunogenic combination of the present invention is likely to be useful for treating both Mtb- (human use), *M. bovis*- and *M. caprae*- (veterinary use) infected subjects.

Immunogenic Combination

In one embodiment, the heterooligomeric mycobacterial partners comprised in or encoded by the immunogenic combination of the present invention are selected from the group of the Esx, PE and PPE mycobacterial antigens. Such groups of mycobacterial gene products are well known in the art and can be easily identified by the skilled person from the data available in the prior art.

For illustrative purpose, the *M. tuberculosis* genome contains 23 Esx genes (named Esx A to W), which encode proteins presumably linked to Mtb virulence. The Esx gene products are typically characterized by a small size of approximately 100 amino acid residues and the presence of a central WXG motif. Biophysical studies indicate that gene products of Esx pairs interact in heterodimers which are likely the functional form of these proteins. Representative examples of such heterodimers include without limitation, e.g. EsxA (ESAT6) and EsxB (CFP-10); EsxG (TB9.8 or Rv0287) and EsxH (TB10.4 or Rv0288); EsxR (Rv3019c) and EsxS (Rv3020c); EsxO (Rv2346c) and EsxP (Rv2347c) and EsxV and EsxW.

The PE and PPE multigene families of *Mycobacterium tuberculosis* comprise about 10% of the coding potential of the genome and account approximately 168 members (for a review see for example Deng and Xie, J Cell Bioch, 2013, 113: 1087-1095). Members of this family are characterized by a conserved N-terminal and a variable C-terminal. The function of the proteins encoded by these large gene families remains unknown, although they have been proposed to be involved in antigenic variation and disease pathogenesis. Representative examples of PE/PPE heterodimers include without limitation, e.g. Rv3478 and Rv3477.

Amino acid sequences of the suitable mycobacterial antigens of the EsX, PE and PPE families and the encoding nucleotide sequences are readily available in specialized data banks and in the literature. For example, Mtb sequences can be found in Cole et al. (1998, Nature 393: 537) or at websites such as those maintained by the Wellcome Trust Sanger Institute, Institut Pasteur and others (e.g. TB database (@tbdb.org) and tuberculist (@tuberculist.epfl.ch)). However, the present invention is not limited to these exemplary *Mycobacterium* species. Indeed the nucleotide and amino acid sequences can vary between different isolates and strains and this natural genetic variation is included within the scope of the invention as well as non-natural modification(s) such as those described herein. When modified, the heterooligomeric partners show preferably a percentage of identity of at least 70% and preferably at least 80% (e.g. 80%, 85%, 90%, 92%, 94%, 95%, 96%, 97%, 98%, 99% or 100%) with the amino acid sequence of their respective native EsX, PE and PPE antigen, over the full length polypeptide or a fragment thereof (e.g. at least 40 amino acid residues). The term "identity" refers to an amino acid to amino acid or nucleotide to nucleotide correspondence between two polypeptide or nucleic acid sequences. The percentage of identity between two sequences is a function of the number of identical positions shared by the sequences, taking into account the number of gaps which need to be introduced for optimal alignment and the length of each gap. Various computer programs and mathematical algorithms are available in the art to determine the percentage of identity between amino acid sequences, such as for example the Blast program available at NCBI or ALIGN in Atlas of Protein Sequence and Structure (Dayhoffed, 1981, Suppl., 3: 482-9). Programs for determining identity between nucleotide sequences are also available in specialized data base (e.g. Genbank, the Wisconsin Sequence Analysis Package, BESTFIT, FASTA and GAP programs).

In the context of the present invention, it can be worth modifying one or both of heterooligomeric partners. Representative examples of suitable modifications include without limitation (a) the deletion of internal highly hydrophobic region(s), and/or (b) the deletion of N-terminal signal peptide (replacement with heterologous ones if needed), and/or (c) the deletion of unfolded region that may interfere negatively with solubility, stability, immunogenicity and recombinant expression and/or (d) the deletion or mutation of a catalytic domain to abolish at least one of the biological activities of the mycobacterial antigen(s) and/or the heterooligomer and/or (e) the deletion or mutation of one or more amino acid residue(s) so as to reduce or abolish its/their interaction of to a target cellular protein (e.g. a mammalian cellular protein which in the context of a Mtb infection is capable of specifically binding to the heterooligomer of the mycobacterial antigen(s) which in the context of Mtb infection permits to the bacteria to decrease, impair or modify the native function or activity of said target cellular protein and thus contribute to the development of the Mtb infection or a disease associated to the Mtb infection) and thus avoid impairment of a cellular activity or a cellular function.

In a preferred aspect, the heterooligomeric mycobacterial antigens are selected from the group consisting of ESAT-6 (Rv3875), CFP10 (Rv3874), PPE60 (Rv3478), PE31 (Rv3477), TB10.4 (Rv0288) and TB9.8 (Rv0287).

In another preferred aspect, such heterooligomeric mycobacterial antigens are fused to form a fusion polypeptide. Representative but not limiting examples of fusions comprised or encoded by the immunogenic combination of the invention includes (a) a fusion of EsxA (also named ESAT-6 or Rv3875) with EsxB (also named CFP10 or Rv3874); (b) a fusion of EsxG (also named TB10.4 or Rv0288) with EsxH (also named TB9.8 or Rv0287) and (c) a fusion of the PE mycobacterial antigen Rv3478 with its heterooligomeric partner PPE mycobacterial antigen Rv3477. In the context of the invention, an immunogenic combination may comprise two or more fusions of heterooligomeric partners (e.g. a fusion of CFP10 with ESAT-6 and a fusion of TB10.4 with TB9.8).

The present invention encompasses fusions in both directions, with one of heterooligomeric partner in N terminal of the fusion or in C terminal. The fusion can be direct or with a linker in between the heterooligomeric partners. A preferred fusion includes CFP10 at the N-terminus and ESAT-6 at the C-terminus. Another preferred fusion includes TB10.4 at the N-terminus and TB9.8 at the C-terminus.

Desirably, the fusion comprised or encoded by the immunogenic composition of the invention does not include any other immunogenic fragment of mycobacterial antigen (although it can include a non-immunogenic fragment of another mycobacterial antigen, e.g. for use as a linker or targeting peptide, etc as described herein).

A particularly preferred immunogenic combination according to the present invention comprises or encodes a fusion polypeptide comprising an amino acid sequence having at least 70% identity with the amino acid sequence shown in SEQ ID NO: 1 or any variant or fragment thereof. More specifically, SEQ ID NO: 1 provides a fusion consisting of CFP10 and ESAT6, wherein the heterooligomeric partners are separated by a 14 amino acid peptide corresponding to the portion 149-162 of the Mtb protein Rv1827 used as a linker.

Another particularly preferred immunogenic combination according to the present invention comprises or encodes a fusion polypeptide comprising an amino acid sequence having at least 70% identity with the amino acid sequence shown in SEQ ID NO: 2 or any variant or fragment thereof. More specifically, SEQ ID NO: 2 provides a fusion consisting of TB10.4 and Rv0287 wherein the heterooligomeric partners are separated by a 13 amino acid peptide corresponding to the portion 149-161 of the Mtb protein Rv1827 used as a linker.

Still another particularly preferred immunogenic combination according to the present invention comprises or encodes a fusion comprising an amino acid sequence having at least 70% identity with the amino acid sequence shown in SEQ ID NO: 1 or any variant or fragment thereof and a fusion comprising an amino acid sequence having at least 70% identity with the amino acid sequence shown in SEQ ID NO: 2 or any variant or fragment thereof.

Further to the heterooligomeric mycobacterial partners (e.g. the fusion thereof), the immunogenic combination of the invention can further comprise or encode one or more additional mycobacterial antigen(s). Said additional mycobacterial antigen(s) is/are preferably selected from the group consisting of antigens of the active, resuscitation and latent phases. Said additional mycobacterial antigen(s) can be comprised in or expressed by the immunogenic combination in the form of separate polypeptides or in the form of one or more fusion polypeptides (e.g. additional fusion polypeptide(s)) or both in the form of separate antigen(s) and fusion(s).

Advantageously, the heterooligomeric partners and eventually the one or more additional mycobacterial antigen(s) comprised in or encoded by the immunogenic combination of the invention are independently obtained from a Mycobacterium species of the tuberculosis complex selected from the group consisting of M. tuberculosis (Mtb), M. bovis, M. bovis BCG, M. africanum, M. canetti, M. caprae, and M. microti, with a specific preference for Mtb.

Suitably, the immunogenic combination of the present invention further comprises or encodes at least two additional mycobacterial antigens. As used herein, "at least two" is a number comprised within a range going from 2 to 30 (i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30). Preferably, the immunogenic combination of the present invention comprises from 2 to 10 additional mycobacterial antigens or corresponding nucleic acid molecules, with a specific preference for 2 to 6.

Desirably, the "one or more additional mycobacterial antigen(s)" are different from each other and different from the (fused) heterooligomeric partners. In the context of the invention, each of the additional mycobacterial antigen(s) can independently be a native mycobacterial antigen (e.g. a full length antigen) or a modified version (fragment or variant) thereof provided that it retains immunogenic properties (e.g. capacity of inducing a cell mediated immune response CD4+ and/or CD8+ and/or an antibody response).

In a preferred embodiment, the one or more additional mycobacterial antigens is/are independently selected from the group consisting of antigens of the active, resuscitation and latent phases.

"Antigens of the active phase" are typically the set of proteins that are mainly expressed when Mycobacterium is actively growing and replicating in vivo. A vast number of active mycobacterial antigens for use in this invention are described in the literature (e.g. Bertholet et al., 2008, J. Immunol. 181: 7948-57; Bertholet and al., 2010, Sci Transl Med 2: 53ra74). Representative examples of mycobacterial antigens of the active phase include but are not limited to Ag85A (Rv3804), Ag85B (Rv1886), Rv3619, Rv3620 and PPE protein Rv2608.

"Antigens of the resuscitation phase" refer to any antigen mainly expressed or involved into the transition between the dormancy and/or persistent state and active growth and replication (active state of Mycobacterium infection). The resuscitation antigens for use in this invention are described in the literature (e.g. Yeremeev et al., 2003, Infection and Immunity 71: 4789-94; Kana et al., 2008, Mol Microbiol 67: 672-84; and Commandeur et al., 2011, Clin Vaccine Immunol. 18: 676-83). Representative examples of mycobacterial antigens of the resuscitation phase include but are not limited to RpfA, RpfB, RpfC, RpfD and RpfE.

"Antigens of the latent phase" are mainly expressed during the dormant (or persistent) phase of the Mycobacterium infection, a reversible state of low metabolic activity in which the Mycobacterium can persist for extended periods. A vast number of latent mycobacterial antigens for use in the present invention are described in the literature. Exemplary Mtb latent antigens are those encoded by the DosR regulon which mediates the bacteria response to hypoxia and starvation antigens that are up-regulated upon depletion of nutrients (Singh et al., 2013, Vaccine, 2013.11.065; WO03/000721; WO03/004520; WO03/035681; WO2004/006952 and WO2006/104389). Representative examples of mycobacterial antigens of the latent phase include but are not limited to Rv0081, Rv0111, Rv0198, Rv0569, Rv1733c, Rv1735, Rv1737, Rv1806, Rv1807, Rv1813, Rv2005c, Rv2029c, Rv2032, Rv2626, Rv2627, Rv2628, Rv2660c, Rv3407 and Rv3812.

Suitably, the immunogenic combination of the present invention is "multiphasic" comprising or encoding mycobacterial antigens, and particularly Mtb antigens, from at least two infection phases (e.g. active and resuscitation, active and latent or resuscitation and latent phases). A particularly appropriate combination comprises or encodes Mtb antigens from the three infection phases with at least one antigen from the active infection phase, at least one antigen from the latent infection phase and at least one antigen from the resuscitation infection phase.

Advantageously, the one or more additional mycobacterial antigen(s) comprised or encoded by the immunogenic combination of the present invention is/are selected from the group consisting of Ag85A (Rv3804), Ag85B (Rv1886), Rv3619, Rv3620, RpfB, RpfD, Rv0081, Rv0111, Rv0198, Rv0569, Rv1733c, Rv1735, Rv1737, Rv1806, Rv1807, Rv1813, Rv2005c, Rv2029c, Rv2032, Rv2626, Rv2627, Rv2628, Rv2660c, Rv3407 and Rv3812. Preferably, said additional mycobacterial antigen(s) is/are selected from the group consisting of Ag85B (Rv1886), RpfB, RpfD, Rv1813, Rv2626 and Rv3407. As for the heterooligomeric mycobacterial antigens, one or more of the additional mycobacterial antigen(s) in use in the immunogenic combination of the present invention can be modified with respect to the corresponding native mycobacterial antigen. Representative examples of suitable mycobacterial antigens for use herein include but are not limited to a Rv1813 antigen (Rv1813*) as set forth in SEQ ID NO: 3 modified with respect to the native counterpart by deletion of the N-terminal signal peptide (from the first residue to about position 31); a Ag85B (Ag85B**) as set forth in SEQ ID NO: 4 modified with respect to the native counterpart by deletion of the N-terminal signal peptide (from the first residue to about position 32).

In a more preferred embodiment, the immunogenic combination comprises or encodes a fusion of the heterooligomeric mycobacterial partners CFP10 and ESAT6 and further comprises or encodes additional mycobacterial antigens Rv2626 and Ag85B. Another preferred immunogenic combination comprises or encodes a fusion of the heterooligomeric partners CFP10 and ESAT-6 and a fusion of the heterooligomeric partners TB10.4 and TB9.8 and further comprises or encodes additional mycobacterial antigens Rv2626, Ag85B, RpfB, RpfD, Rv3407 and Rv1813. Another preferred immunogenic combination comprises or encodes heterooligomeric partners CFP10 and ESAT-6 and further comprises or encodes additional mycobacterial antigens Rv2626, Ag85B, RpfB, and RpfD. Still another preferred immunogenic combination comprises or encodes heterooligomeric partners Rv0287 and TB10.4 as well as Rv3478 and Rv3477 and further comprises or encodes additional mycobacterial antigen Rv3407.

In another embodiment, the present invention encompasses any arrangement of the mycobacterial antigens comprised or encoded by the immunogenic combination. In this respect, the additional mycobacterial antigens may be present or expressed in the form of separate polypeptides (e.g. a mixture of recombinantly produced Mtb antigens) or in the form of one or more fusion polypeptide(s) (covalent linkage of at least two of the additional mycobacterial antigens) or both separate antigen(s) and fusion(s). In other words, such additional mycobacterial antigens may be expressed independently (under separate regulatory elements) or as fusion of at least two antigens (e.g. by covalent linkage of the encoding nucleic acid molecules). Moreover, the encoding nucleic acid molecules can be carried by one or more vector(s). In this regard, one may use the same type of vectors (e.g. two MVA) or different type of vectors (e.g. a plasmid DNA and a MVA) to express the various mycobacterial antigens or fusion(s) described herein.

Fusion Polypeptide(s)

In a preferred embodiment, the additional mycobacterial antigens are comprised or encoded by the immunogenic combination of the invention in the form of fusion of two.

Exemplary fusion polypeptides of additional mycobacterial antigens comprise Rv2626 and Ag85B; RpfB and RpfD; and Rv3407 and Rv1813 (or any variant or fragment thereof). As for the fusion of the heterooligomeric partners, any arrangement is possible in the context of the present invention. For illustrative purpose, a fusion comprising Rv3407 and Rv1813 can be with Rv3407 at the N-terminus (Rv3407/1813), internally or at the C-terminus (Rv1813/Rv3407).

The fusion polypeptide(s) of heterooligomeric mycobacterial partners and/or of the additional mycobacterial antigens may also comprise one or more other component(s), which may derive from a *Mycobacterium* species (e.g. additional mycobacterial antigen(s)) or be heterologous (i.e. from a source different of a *Mycobacterium*). It/they may be immunogenic but it is preferred that it/they are not. Examples of such additional components include without any limitation linker, cleavage site(s), tag peptide(s), targeting peptide(s), trans-membrane domain(s), oligomerization domain(s). Depending on the mycobacterial antigen, the presence of such peptide(s) may be beneficial for enhancing expression, folding and/or immunogenicity of the resulting antigen or fusion when compared with antigen or fusion expressed without such peptides. Enhanced expression may be determined by conventional techniques such as Western blotting. Enhanced folding may be determined by conventional techniques such as size exclusion chromatography (to discriminate soluble versus aggregated proteins). Enhanced immunogenicity may be determined using conventional assays such as ELISpot assay.

For example, it may be advantageous to insert a cleavage site between the upstream and downstream polypeptides comprised in the fusion polypeptide(s) described herein (the fusion of heterooligomeric partners and/or of additional mycobacterial antigens). Suitable cleavage sites for use in the present invention include but are not limited to the foot and mouth disease virus 2A peptide (F2A; SEQ ID NO: 5), the *Thosea asigna* virus 2A peptide (T2A; SEQ ID NO: 6) and the *Equine rhinitis* A virus peptide (E2A; SEQ ID NO: 7) which have self-cleavage activities. Such peptides 2A mediate a co-translational cleavage at their own C-terminus and it is proposed to manipulate the ribosome into skipping the synthesis of a specific peptide bond-producing a discontinuity in the peptide backbone- (Luke, 2012. Innovations in Biotechnology, Dr. Eddy C. Agbo (Ed.), ISBN: 978-953-51-0096-6, In Tech, Available from: www.intechopen.com). The resultant fusion protein would thus be expected to produce the upstream mycobacterial antigen fused to the cleavage site-containing linker and the downstream mycobacterial antigen.

Alternatively or in addition, any of the mycobacterial antigen(s) in use herein or fusion thereof may comprise targeting peptide(s) such as signal and/or trans-membrane peptides. Such targeting peptides are well known in the art (see for example WO99/03885). Briefly, signal peptides (SS) are generally present at the N-terminus of membrane-presented or secreted polypeptides and initiate their passage into the endoplasmic reticulum (ER). They comprise 15 or more essentially hydrophobic amino acids which are then removed by a specific ER-located endopeptidase to give the mature polypeptide. Trans-membrane peptides (TM) are usually highly hydrophobic in nature and serve to anchor the polypeptides in the cell membrane. The choice of the trans-membrane and/or signal peptides which can be used in the context of the present invention is vast. They may be obtained from any membrane-anchored and/or secreted polypeptide (e.g. cellular or viral polypeptides) such as those of immunoglobulins, tissue plasminogen activator (tPA), insulin, rabies glycoprotein, the HIV virus envelope glycoprotein or the measles virus F protein or may be synthetic. The preferred site of insertion of the signal peptide is the N-terminus downstream of the codon for initiation of translation and that of the trans-membrane peptide is the C-terminus, for example immediately upstream of the stop codon.

Alternatively or in addition, any of the mycobacterial antigen(s) in use herein or fusion thereof may comprise a tag peptide(s) in order to facilitate its isolation and detection or to facilitate identification of host cells expressing such antigen or fusion. A vast variety of tag peptides can be used in the context of the invention including without limitation PK tag, FLAG tag, MYC tag, polyhistidine tag (usually a stretch of 5 to 10 histidine residues). Tag peptides can be detected by immunodetection assays using anti-tag antibodies as described in the appended examples. The tag peptide(s) may be independently positioned at the N-terminus of the mycobacterial antigen or fusion (tag-polypeptide) or alternatively at its C-terminus (polypeptide-tag) or alternatively internally or at any of these positions when several tags are employed.

Exemplary fusions of additional mycobacterial antigens for use in the present invention include without limitation polypeptides comprising, or alternatively consisting essentially of, or alternatively consisting of an amino acid sequence which exhibits at least 70% identity, advantageously at least 80% identity, desirably at least 90% identity, preferably at least 95% identity, and more preferably 98% identity and even more preferably 100% identity with any of the amino acid sequences shown in SEQ ID NO: 8 to 12. More specifically, SEQ ID NO: 8 represents a fusion of RpfB and RpfD resuscitation antigens comprising RpfB modified with respect to the native counterpart by deletion of the signal peptide (from the first residue to approximately residue in position 29, and by deletion of the catalytic domain, thus retaining RfpB from approximately position 30 to position 283) fused to the so-called LD (for lysozyme domain) of RpfD antigen with three mutations aimed at abolishing the associated enzymatic activity (e.g. E292K, T315A and Q347A). SEQ ID NO: 9 and SEQ ID NO: 10 describes the fusion of Rv2626 with Ag85B with (SEQ ID NO: 9: Rv2626/2A/Ag85B) or without (SEQ ID NO: 10: Rv2626/Ag85B**) T2A cleavage site. SEQ ID NO: 11 describes the fusion Rv3407/E2A/Rv1813* and SEQ ID NO: 12 the fusion polypeptide Rv3407/Rv1813* without E2A cleavage site.

Typically, the immunogenic combination of the invention can be prepared using standard techniques. For example, mycobacterial antigens may be purified e.g. from bacteria culture or produced recombinantly in a host cell using any of the expression system available in the art or can be provided to the subject upon cloning of the encoding nucleic acid molecule into suitable expression vector(s) in the way described herein.

In addition, the immunogenic combination of the invention may further comprise one or more immunoactivator peptides/polypeptides capable of enhancing immunogenic properties. One may cite for example calreticulin (Cheng et al., 2001, J. Clin. Invest. 108: 669), Mtb heat shock protein 70 (HSP70) (Chen et al., 2000, Cancer Res. 60: 1035), ubiquitin (Rodriguez et al., 1997, J. Virol. 71: 8497), and T helper epitope(s) such as Pan-Dr peptide (Sidney et al., 1994, Immunity 1: 751), pstS1 GCG epitope (Vordermeier et al., 1992, Eur. J. Immunol. 22: 2631), tetanus toxoid peptides P2TT (Panina-Bordignon et al., 1989, Eur. J. Immunol. 19: 2237), P30TT (Demotz et al., 1993, Eur. J. Immunol. 23: 425), hemaglutinin epitope (Rothbard et al., 1989, Int. Immunol. 1: 479) and C4 bp oligomerization domain (Spencer et al., 2012, PLos One 7:e33555). Such immunoactivator peptides/polypeptide(s) may be present or expressed independently or included in the fusion of the heterooligomeric partners and/or of the additional mycobacterial antigens.

Nucleic Acid Molecules and Nucleic Acid Combinations

The present invention also provides nucleic acid molecule combination comprised in the immunogenic combination of the invention as well as isolated nucleic acid molecules encoding said fusion(s) of the mycobacterial heterooligomeric partners and/or of additional mycobacterial antigens.

Within the context of the present invention, the terms "nucleic acid", "nucleic acid molecule", "polynucleotide" and "nucleotide sequence" are used interchangeably and define a polymer of any length of either polydeoxyribonucleotides (DNA) (e.g., cDNA, genomic DNA, plasmids, vectors, viral genomes, isolated DNA, probes, primers and any mixture thereof) or polyribonucleotides (RNA) (e.g., mRNA, antisense RNA) or mixed polyribo-polydeoxyribonucleotides. They encompass single or double-stranded, linear or circular, natural or synthetic nucleic acids.

As defined before, the nucleic molecules of the invention may be native nucleic acids (e.g. isolated from a genome or genomic fragment of a *Mycobacterium*) or may be modified by man to include substitution, deletion, addition and/or insertion of one or more nucleotide(s). The present invention encompasses any modifications aimed to improve cloning and/or expression of the encoded polypeptide(s) and fusion (s) as well as its folding, stability and/or immunogenicity. When several modifications are contemplated, they can concern consecutive and/or non-consecutive nucleotide residues. The modification(s) contemplated by the present invention encompass silent modifications that do not change the amino acid sequence of the encoded mycobacterial antigens and fusion polypeptides, as well as modifications that are translated into the encoded polypeptide. Preferably the modifications do not decrease the immunogenic potential of the resultant polypeptide with respect to the non-modified ones. Representative examples of modifications include but are not limited to introduction of appropriate restriction sites, sequence degeneration (e.g. to reduce sequence homology between nucleic acid molecule(s) used in the context of the invention or in the host cell which may favor genetic instability) and/or optimisation of nucleotide sequence (e.g. to optimize translation in a given host cell) and/or suppression of potentially negative elements (which are expected to negatively influence expression levels).

For example, it may be worth optimizing codon usage for ensuring high level of expression of the encoded gene product in a particular host cell or subject. It has been indeed observed that, when more than one codon is available to code for a given amino acid, the codon usage patterns of organisms are highly non-random and the utilisation of codons may be markedly different between different hosts. As the nucleotide sequences used in the invention are mostly of bacterial origin, they may have an inappropriate codon usage pattern for efficient expression in host cells such as higher eukaryotic cells. Typically, codon optimisation is performed by replacing one or more "native" (mycobacterial) codon corresponding to a codon infrequently used in the host cell of interest by one or more codon encoding the same amino acid which is more frequently used. It is not necessary to replace all native codons corresponding to infrequently used codons since increased expression can be achieved even with partial replacement. Moreover, some deviations from strict adherence to optimised codon usage may be made to accommodate the introduction of restriction site(s) into the resulting nucleic acid molecule.

A particularly preferred embodiment of the present invention is directed to nucleic acid molecules encoding any of the fusion polypeptides set forth in SEQ ID NO: 1, 2 and 8 to 12, with a specific preference for a nucleic acid molecule comprising (alternatively essentially consisting of or alternatively consisting of) a nucleotide sequence which exhibits at least 80% identity, advantageously at least 85% of identity, preferably at least 90% of identity, more preferably at least 95% of identity, and even more preferably 100% identity with any of the nucleotide sequences shown in SEQ ID NO: 13 to 19 or any variant and fragment thereof.

The nucleic acid molecules of the present invention can be generated using sequence data accessible in the art and the sequence information provided herein. For example, they may be isolated using routine techniques well known in the art, e.g. by PCR isolation and/or cloning by conventional molecular biology from a *Mycobacterium* genome of a particular species or genomic fragment thereof, cDNA and genomic libraries or any prior art vector known to include it. Alternatively, the nucleic acid molecules of the invention can also be generated by chemical synthesis in automatised process (e.g. assembled from overlapping synthetic oligonucleotides).

Another embodiment of the invention pertains to fragments of the nucleic acid molecules of the invention, e.g. restriction endonuclease and PCR-generated fragments.

Such fragments can be used as probes, primers or fragments encoding relevant immunogenic portion(s).

Vectors

The present invention also concerns vectors comprising one or more nucleic acid molecule(s) of the present invention (encoding said fusion of the heterooligomeric mycobacterial antigens and/or said fusion polypeptide of additional mycobacterial antigens) as well as compositions comprising such vector(s).

The term "vector" as used herein refers to a vehicle, preferably a nucleic acid molecule or a viral particle that contains the elements necessary to allow delivery, propagation and/or expression of any of the nucleic acid molecule(s) described herein within a host cell or subject. This term encompasses vectors for maintenance (cloning vectors) or vectors for expression in various host cells or subjects (expression vectors), extrachromosomal vectors (e.g. multicopy plasmids) or integration vectors (e.g. designed to integrate into the host cell genome and produce additional copies of the nucleic acid molecules when the host cell replicates) as well as shuttle vectors (e.g. functioning in both prokaryotic and/or eukaryotic hosts) and transfer vectors (e.g. for transferring nucleic acid molecule(s) in a viral genome). For the purpose of the invention, the vectors may be of naturally occurring genetic sources, synthetic or artificial, or some combination of natural and artificial genetic elements.

In the context of the invention, the term "vector" has to be understood broadly as including plasmid and viral vectors. Vectors which are appropriate in the context of the present invention, include, without limitation, bacteriophage, plasmid or cosmid vectors for expression in prokaryotic host cells such as bacteria (e.g. *E. coli*, BCG or *Listeria*); vectors for expression in yeast (e.g. *Saccharomyces cerevisiae, Schizosaccharomyces pombe, Pichia pastoris*); baculovirus vectors for expression in insect cell systems (e.g. Sf 9 cells); as well as plasmid and viral vectors for expression in higher eukaryotic cells or subjects. Typically, such vectors are commercially available (e.g. in Invitrogen, Stratagene, Amersham Biosciences, Promega, etc.) or available from depositary institutions such as the American Type Culture Collection (ATCC, Rockville, Md.) or have been the subject of numerous publications describing their sequence, organization and methods of producing, allowing the artisan to apply them. The present invention also encompasses vectors (e.g. plasmid DNA) complexed to lipids or polymers to form particulate structures such as liposomes, lipoplexes or nanoparticles.

A "plasmid vector" as used herein refers to a replicable DNA construct. Usually plasmid vectors contain selectable marker genes that allow host cells carrying the plasmid vector to be selected for or against in the presence of a corresponding selective drug. A variety of positive and negative selectable marker genes are known in the art. By way of illustration, an antibiotic resistance gene can be used as a positive selectable marker gene that allows a host cell to be selected in the presence of the corresponding antibiotic. Representative examples of suitable plasmid vectors include, without limitation, pREP4, pCEP4 (Invitrogen), pCI (Promega), pVAX (Invitrogen) and pGWiz (Gene Therapy System Inc).

The term "viral vector" as used herein refers to a nucleic acid vector that includes at least one element of a virus genome and may be packaged into a viral particle or to a viral particle. The terms "virus", "virions", "viral particles" and "viral vector particle" are used interchangeably to refer to viral particles that are formed when the nucleic acid vector is transduced into an appropriate cell or cell line according to suitable conditions allowing the generation of viral particles. In the context of the present invention, the term "viral vector" has to be understood broadly as including nucleic acid vector (e.g. DNA viral vector) as well as viral particles generated thereof. The term "infectious" refers to the ability of a viral vector to infect and enter into a host cell or subject. Viral vectors can be replication-competent or -selective (e.g. engineered to replicate better or selectively in specific host cells), or can be genetically disabled so as to be replication-defective or replication-impaired.

Representative examples of suitable viral vectors are generated from a variety of different viruses (e.g. retrovirus, adenovirus, adenovirus-associated virus (AAV), poxvirus, herpes virus, measles virus, foamy virus, alphavirus, vesicular stomatis virus, etc). As described above, the term "viral vector" encompasses vector DNA, genomic DNA as well as viral particles generated thereof, and especially infectious viral particles.

In one embodiment, the viral vector employed in this invention is replication-defective or replication-impaired which means that it cannot replicate to any significant extent in normal cells (e.g. normal human cells) or in the subject to whom it is administered (the impairment or defectiveness of replication functions can be evaluated by conventional means—e.g. via measuring DNA synthesis and/or viral titre in non-permissive cells). Such replication-defective or impaired vectors typically require for propagation, permissive cell lines which bring up or complement the missing/impaired functions.

Examples of viral vectors that are useful in the context of the invention include adenoviral vectors which have a number of well-documented advantages for vaccination, immunotherapy, gene transfer or for recombinant production (for a review, see "Adenoviral vectors for gene therapy", 2002, Ed D. Curiel and J. Douglas, Academic Press). The adenoviral vectors of the present invention can be derived from a variety of human or animal sources (e.g. canine, ovine, simian adenovirus, etc). Any serotype can be employed with a special preference for human adenoviruses and a specific preference for subgenus C such as Ad2, Ad5, Ad6, and subgenus B such as Ad11, Ad34 and Ad35. It may also be advantageous to use animal Ad with a special preference for chimp Ad, such as chimp Ad3 and Ad63. The cited adenovirus are available from ATCC or have been the subject of numerous publications describing their sequence, organization and methods of producing, allowing the artisan to apply them (see for example U.S. Pat. Nos. 6,136,594; 6,133,028; WO00/50573; WO00/70071; WO2004/083418; WO2004/097016 and WO2005/071093).

Preferred replication-defective adenoviral vectors are E1-defective with an E1 deletion extending from approximately positions 459 to 3328 or from approximately positions 459 to 3510 (by reference to the sequence of Ad5 disclosed in the GeneBank under the accession number M 73260). The cloning capacity can further be improved by deleting additional portion(s) of the adenoviral genome (all or part of the non-essential E3 region (e.g. deletion from approximately positions 27867 to 30743) or of other essential E2 and/or E4 regions as described in WO94/28152 and Lusky et al., 1998, J. Virol 72: 2022).

The nucleic acid molecules of the present invention can be independently inserted in any location of the adenoviral genome, with a specific preference for insertion in replacement of the E1 and/or E3 region. They may be positioned in sense or antisense orientation relative to the natural transcriptional direction of the region in question.

Other examples of viral vectors particularly appropriate in the context of the invention include poxvirus vectors such as fowlpox vectors (e.g. FP9), canarypox vectors (e.g. ALVAC) and vaccinia virus vectors, the latter being preferred. Suitable vaccinia viruses include without limitation the Copenhagen strain, the Wyeth strain, NYVAC (U.S. Pat. No. 5,494,807) and the modified Ankara (MVA) strain (Antoine et al., 1998, Virol. 244: 365; WO02/42480). The general conditions for constructing and producing recombinant poxvirus are well known in the art (see for example WO2010/130753; WO03/008533; U.S. Pat. Nos. 6,998,252; 5,972,597 and 6,440,422). The nucleic acid molecules of the present invention are preferably inserted within the poxviral genome in a non-essential locus. Thymidine kinase gene is particularly appropriate for insertion in Copenhagen vaccinia vectors and deletion II or III for insertion in MVA vector (WO97/02355).

Other viral vectors suitable in the context of the invention are morbillivirus which can be obtained from the paramyxoviridae family, with a specific preference for measles virus. Various attenuated strains are available in the art (Brandler et al, 2008, CIMID, 31: 271; Singh et al., 1999, J. virol. 73(6): 4823), such as and without limitation, the Edmonston A and B strains (Griffin et al., 2001, Field's in Virology, 1401-1441), the Schwarz strain (Schwarz A, 1962, Am J Dis Child, 103: 216), the S-191 or C-47 strains (Zhang et al., 2009, J Med Virol. 81 (8): 1477). Insertion between P and M genes or between H and L genes is particularly appropriate.

Suitable vector for use in the present invention also include bacterium cell which can be wild-type or mutant (e.g. avirulent). Well-known examples of such bacterium cells include without limitation avirulent *Mycobacterium* (e.g. *Mycobacterium bovis* BCG), *Lactobacillus* (e.g. *Lactococcus lactis*), *Listeria* (e.g. *Listeria monocytogenes*) and other microorganisms such as *Salmonella* and *Pseudomona*. A preferred embodiment is directed to a BCG vector into the genome of which has been incorporated nucleic acid molecule(s) encoding one or more mycobacterial antigen(s) or fusion polypeptide(s) as defined above in a manner allowing the BCG vector to express such element(s).

In one embodiment, the nucleic acid molecules comprised in the immunogenic combination of the invention are carried out by a single vector. Alternatively they can be carried by two or more vectors which can be administered to the subject simultaneously, or sequentially.

In accordance with the present invention, the nucleic acid molecules comprised in the vector of the invention are in a form suitable for expression in a host cell or subject, which means that the nucleic acid molecules set forth herein are operably linked to appropriate regulatory sequences. As used herein, the term "regulatory elements" or "regulatory sequence" refers to any element that allows, contributes or modulates the expression of nucleic acid molecule(s) in a given host cell or subject, including replication, duplication, transcription, splicing, translation, stability and/or transport of the nucleic acid(s) or its derivative (i.e. mRNA). It will be appreciated by those skilled in the art that the choice of the regulatory sequences can depend on such factors as the vector itself, the host cell or subject, the level of expression desired, etc. "Operably linked" means that the elements being linked are arranged so that they function in concert for their intended purposes. For example a promoter is operably linked to a nucleic acid molecule if the promoter effects transcription from the transcription initiation to the terminator resulting in the expression of the coding sequence present in the nucleic acid molecule in a permissive host cell.

In particular, the nucleotide acid molecules comprised in the immunogenic combination of the present invention are placed under the transcriptional control of a promoter suitable for ensuring expression of the encoded polypeptide(s) and/or fusion(s) and eventually of the additional mycobacterial antigen(s) in a mammalian cell. In the context of the invention, the promoter can be constitutive directing expression of the operably linked nucleic acid molecule in many types of host cells or specific to certain host cells (e.g. lung-specific regulatory sequences) or regulated in response to specific events or exogenous factors (e.g. by temperature, nutrient additive, hormone, etc) or according to the phase of a viral cycle (e.g. late or early). One may also use promoters that are repressed during the production step in response to specific events or exogenous factors, in order to optimize vector production and circumvent potential toxicity of the expressed polypeptide(s).

Promoters suitable for constitutive expression in mammalian cells include but are not limited to the cytomegalovirus (CMV) immediate early promoter (U.S. Pat. No. 5,168,062), the RSV promoter, the adenovirus major late promoter, the phosphoglycero kinase (PGK) promoter, the thymidine kinase (TK) promoter of herpes simplex virus (HSV)-1 and the T7 polymerase promoter. Promoters such as the trp, lac, phage promoters, tRNA promoters and glycolytic enzyme promoters may be used in prokaryotic hosts. Useful yeast promoters include the promoter regions for metallothionein, 3-phosphoglycerate kinase or other glycolytic enzymes such as enolase or glyceraldehyde-3-phosphate dehydrogenase, enzymes responsible for maltose and galactose utilization. Vaccinia virus promoters are particularly adapted for expression in poxviral vectors. Representative examples include without limitation the vaccinia 7.5K, H5R, B2R, A35R, 11K7.5 (Erbs et al., 2008, Cancer Gene Ther. 15: 18), TK, p28, p11 and K1L promoter, as well as synthetic promoters such as those described in Chakrabarti et al. (1997, Biotechniques 23: 1094-7; Hammond et al., 1997, J. Virol Methods 66: 135-8; and Kumar and Boyle, 1990, Virology 179: 151-8) as well as early/late chimeric promoters (e.g. pSE/L). Promoters suitable for measles-mediated expression include without limitation any promoter directing expression of measles transcription units (Brandler and Tangy, 2008, CIMID 31: 271).

Those skilled in the art will appreciate that the regulatory elements controlling the expression of the nucleic acid molecule(s) of the invention may further comprise additional elements for proper initiation, regulation and/or termination of transcription (e.g. polyA transcription termination sequences), mRNA transport (e.g. nuclear localization signal sequences), processing (e.g. splicing signals), and stability (e.g. introns and non-coding 5' and 3' sequences), translation (e.g. an initiator Met, tripartite leader sequences, IRES ribosome binding sites, Shine-Dalgarno sequences, etc.) into the host cell or subject and purification steps (e.g. a tag as described herein).

Particularly preferred embodiments of the invention are directed to a vector (or viral particle thereof) selected from the group consisting of:
  (i) A vector comprising a nucleic acid molecule encoding a fusion comprising heterooligomeric partners ESAT-6 and CFP10, a nucleic acid molecule encoding Ag85B and a nucleic acid molecule encoding Rv2626;
  (ii) A vector comprising a nucleic acid molecule encoding a fusion comprising heterooligomeric partners ESAT-6 and CFP10; a nucleic acid molecule encoding a fusion comprising heterooligomeric partners TB10.4 and TB9.8, a nucleic acid molecule encoding a fusion polypeptide comprising the additional mycobacterial antigens Rv2626 and Ag85B; a nucleic acid molecule encoding a fusion polypeptide comprising the additional mycobacterial antigens RpfB and RpfD; and a nucleic acid molecule encoding a fusion polypeptide comprising the additional mycobacterial antigens Rv3407 and Rv1813 (as illustrated by MVATG18598 in the appended examples); and (iii) A vector comprising a combination of nucleic acid molecules encoding heterooligomeric partners ESAT-6 and CFP10, and additional mycobacterial antigens Ag85B, Rv2626, RpfB and RpfD (as illustrated by MVATG18597 in the appended examples).

More preferably, the vector described above is a MVA vector.

According to a preferred embodiment, the vector of the invention is in the form of infectious viral particles. Typically, such viral particles are produced by a process comprising the steps of (i) introducing the viral vector of the invention into a producer cell, (ii) culturing said producer cell under suitable conditions allowing the production of said infectious viral particle, (iii) recovering the produced viral particle from the culture of said producer cell, and (iv) optionally purifying said recovered viral particle.

When the viral vector is replication-defective or replication-impaired, the particles are usually produced in a permissive producer cell or via the use of a helper virus, which supplies in trans the missing/impaired functions. For example, suitable producer cells for complementing E1-deleted adenoviral vectors include the 293 cells (Graham et al., 1997, J. Gen. Virol. 36: 59-72) as well as the HER-96 and PER-C6 cells (e.g. Fallaux et al., 1998, Human Gene Ther. 9: 1909-17; WO97/00326) or any derivative of these cell lines. Avian cells are particularly suitable for propagating poxvirus vectors including without limitation primary chicken embryo fibroblasts (CEF) prepared from chicken embryos obtained from fertilized eggs, and duck cell lines (e.g. as described in WO03/076601, WO2009/004016, WO2010/130756 and WO2012/001075).

The infectious viral particles may be recovered from the culture supernatant and/or from the producer cells after lysis. They can be further purified according to standard techniques (chromatography, ultracentrifugation techniques, etc).

The present invention also encompasses vectors or viral particles that have been modified to allow preferential targeting to a specific host cell. A characteristic feature of targeted vectors is the presence at their surface of a ligand capable of recognizing and binding to a cellular and surface-exposed component such as a cell-specific marker (e.g. a 30 *Mycobacterium*-infected cell), a tissue-specific marker (e.g. a lung-specific marker), etc. Examples of suitable ligands include antibodies or fragments thereof directed to a mycobacterial antigenic domain. Targeting can be carried out by genetically inserting the ligand into a polypeptide present on the surface of the virus (e.g. adenoviral fiber, penton, pIX or vaccinia p14 gene product).

Host Cells and Production Methods

In another aspect, the invention also relates to host cells which comprise the immunogenic combinations, the fusion polypeptides, the nucleic acid molecules or vectors (e.g. viral particles) of the invention as well as compositions comprising such a host cell.

As used herein, the term "host cell" should be understood broadly without any limitation concerning particular organization in tissue, organ, or isolated cells. Such cells may be of a unique type of cells or a group of different types of cells such as cultured cell lines, primary cells and proliferative cells. The invention encompasses prokaryotic host cells, lower eukaryotic host cells such as yeast, and other eukaryotic host cells such as insect cells, plant and mammalian (e.g. human or non-human) cells as well as producer cells capable of producing the vector of the invention (e.g. 293, HER96, PERC.6 cells, CEF, duck cell lines, etc). This term also includes cells which can be or has been the recipient of the vector described herein as well as progeny of such cells.

According to a specific embodiment of the invention, the host cell can be further encapsulated. Cell encapsulation technology is known in the art.

Still a further aspect of the present invention is a method for recombinant production of the mycobacterial antigens (e.g. fusion(s) of heterooligomeric partners and/or additional mycobacterial antigen(s)) comprised in or encoded by the immunogenic combination, employing the vectors (or infectious viral particles) and/or host cells of the invention. Typically, the method comprises the steps of (i) introducing a vector into a suitable host cell to produce a transfected or infected host cell, (ii) culturing in-vitro said transfected or infected host cell under conditions suitable for growth of the host cell, (iii) recovering the cell culture, and (iv) optionally, purifying the mycobacterial antigen(s) recovered from the cell culture.

It is expected that those skilled in the art are knowledgeable of the numerous expression systems available in the art for expressing polypeptides and of the methods for introducing a vector into a host cell. Such methods include, but are not limited to microinjection, $CaPO_{4\_}$ mediated transfection, DEAE-dextran-mediated transfection, electroporation, lipofection/liposome fusion, gene guns, transduction, viral infection as well as direct administration into a host organism via various means. The method may also be used in association with conventional transfection reagents that facilitate introduction of nucleic acids in host cells, such as polycationic polymers (e.g. chitosan, polymethacrylate, PEI, etc) and cationic lipids (e.g. DC-Chol/DOPE, transfectam, lipofectin, etc).

Host cells can be cultured in conventional fermentation bioreactors, flasks, and petri plates. Culturing can be carried out at a temperature, pH and oxygen content appropriate for a given host cell. No attempts will be made here to describe in detail the various prokaryotic and eukaryotic expression systems available in the art for such purposes.

In a preferred embodiment, the method employs an *E coli* host cell and in particular a *E. coli* strain carrying the D13 prophage in its genome for allowing inducible expression of T7 polymerase by lactose or analogue of lactose (e.g. IPTG: IsoPropyl b-D-1-Thio Galactopyranoside). Such strains are available for various manufacturers (e.g. Lucigen, Merck, etc). After plasmid introduction, the transformed *E. coli* cell can be cultured at a temperature comprised between approximately 18° C. to approximately 39° C. (specific preference for approximately 30° C. or approximately 37° C.) for a time period varying from 6 to 48 hours (specific preference from approximately 8 to approximately 24h) in conventional medium adapted to the vector selection marker (e.g. presence of antibiotic) and to the host strain (e.g. in the presence of an inducer such as IPTG). The cell culture is recovered and can be lysed (e.g. chemical lysis with a detergent, sonication, etc). After centrifugation of the cell lysate, both the supernatant and the pellet can be collected for further analysis (e.g. by SDS PAGE) to evaluate the level of expression as well as the solubility of the expressed material (e.g. soluble material can be found in the cell lysate supernatant and insoluble material can be trapped in inclusion bodies).

The mycobacterial antigen(s) and/or fusion thereof can be recovered from the culture supernatant and/or from the host cell (e.g. upon cell lysis). The recovered materiel can optionally be purified by well-known purification methods including ammonium sulfate precipitation, acid extraction, gel electrophoresis; filtration and chromatographic methods (e.g. reverse phase, size exclusion, ion exchange, affinity, hydrophobic-interaction, hydroxyapatite, high performance liquid chromatography, etc). The conditions and techniques to be used depend on factors such as net charge, molecular weight, hydrophobicity, hydrophilicity and will be apparent to those having skill in the art. Moreover, the level of purification will depend on the intended use. For example protein concentration can be evaluated by Bradford assay (Biorad), endotoxin levels can be evaluated by techniques such as the Portable Test System (Charles River Laboratories) and the mass of the purified polypeptides can be measured using MALDI (Matrix-Assisted Laser Desorption/Ionisation) or electrospray methods.

Compositions

In another aspect, this invention provides a composition comprising at least one of the immunogenic combination, fusion polypeptide, nucleic acid molecule, vector(s) (e.g. infectious viral particle), or host cell described herein (also referred herein to "active agent") or any combination thereof (e.g. combination of different polypeptides or vectors/viral particles). Preferably, the composition is a pharmaceutical composition which comprises further to a therapeutically effective amount of the active agent(s), one or more pharmaceutically acceptable vehicle(s).

As used herein, a "pharmaceutically acceptable vehicle" is intended to include any and all carriers, solvents, diluents, excipients, adjuvants, dispersion media, coatings, antibacterial and antifungal agents, and absorption delaying agents, and the like, compatible with administration in a subject and in particular in a human.

As used herein a "therapeutically effective amount" is a dose sufficient for the intended use. When prophylactic use is concerned, this term means a dose sufficient to prevent or to delay the onset and/or establishment of a *Mycobacterium* infection (e.g. Mtb infection). For "therapeutic" use, the composition is administered to a subject already infected with a *Mycobacterium* species with the goal of treating active disease or preventing reactivation in latently infected individuals, eventually in combination with one or more conventional therapeutic modalities. In particular, a therapeutically effective amount of the composition of the invention could be that amount necessary to cause induction or stimulation of the immune system in the administered subject (e.g. resulting in the development of an innate and/or specific response).

The subject to be treated may be a newborn, an infant, a young adult or an adult. The subject may have been previously immunized with *Bacillus* Calmette-Guérin (BCG) or previously treated for a *Mycobacterium* infection before being treated with the active agent(s) described herein. It may or not be co-infected with another pathogenic organism (e.g. the human immunodeficiency virus HIV).

In particular, the subject to be treated is infected with a virulent *Mycobacterium* species (e.g. Mtb) which may be a drug resistant (e.g. MDR, XDR or TDR) strain. The infecting *Mycobacterium* can be the same strain or isolate as any of the *Mycobacterium* from which originate the antigens comprised or encoded by the active agent used in the present invention or it can be from a different strain or isolate.

The composition of the invention is suitably buffered in order to be appropriate for human or animal use at a physiological or slightly basic pH (e.g. from approximately pH 7 to approximately pH 9). Suitable buffers include without limitation phosphate buffer (e.g. PBS), bicarbonate buffer and/or Tris buffer.

The composition of the invention can further comprise a diluent appropriate for human or animal use. It is preferably isotonic, hypotonic or weakly hypertonic and has a relatively low ionic strength. Representative examples include sterile water, physiological saline (e.g. sodium chloride), Ringer's solution, glucose, trehalose or saccharose solutions, Hank's solution, and other aqueous physiologically balanced salt solutions (see for example the most current edition of Remington: The Science and Practice of Pharmacy, A. Gennaro, Lippincott, Williams & Wilkins).

Additional pharmaceutically acceptable excipients may be used for providing desirable pharmaceutical or pharmacodynamic properties, including for example modifying or maintaining the pH, osmolarity, viscosity, clarity, colour, sterility, stability, rate of dissolution of the formulation, modifying or maintaining release or absorption into an the human or animal organism, promoting transport across the blood barrier or penetration in a particular organ (e.g. lung).

In addition, the composition of the invention may comprise one or more adjuvant(s) suitable for systemic or mucosal application in humans. Preferably, the adjuvant is capable of stimulating immunity to the composition of the invention, especially a T cell-mediated immunity e.g. through the toll-like receptors (TLR), such as TLR-7, TLR-8 and TLR-9. Representative examples of useful adjuvants include without limitation alum, mineral oil emulsion such as Freunds complete and incomplete (IFA), lipopolysaccharide or a derivative thereof (Ribi et al., 1986, Immunology and Immunopharmacology of Bacterial Endotoxins, Plenum Publ. Corp., NY, p407-419), saponins such as QS21 (WO 98/56415), imidazo-quinoline compounds such as Imiquimod (WO2007/147529), cytosine phosphate guanosine oligodeoxynucleotides such as CpG and cationic peptides such as IC-31 (Kritsch et al., 2005, J. Chromatogr Anal. Technol Biomed Life Sci 822: 263) or any derivative thereof.

The pharmaceutically acceptable vehicles included in the composition of the invention must also permit to preserve its stability under the conditions of manufacture and long-term storage (i.e. at least one month with a preference for at least one year) at freezing (e.g. −70° C., −20° C.), refrigerated (e.g. 4° C.), ambient temperatures. Such "long term" formulations are known in the art (e.g. WO98/02522; WO03/053463). One may cite (a) 1M saccharose, 150 mM NaCl, 1 mM MgCl$_2$, 54 mg/l Tween 80, 10 mM Tris pH 8.5, (b) 10 mg/ml mannitol, 1 mg/ml HSA, 20 mM Tris, pH 7.2, and 150 mM NaCl and (c) physiological saline which are particularly adapted to the composition of the invention.

The composition of the invention can be in various forms, e.g. solid, liquid or frozen. Solid (e.g. dry powdered or lyophilized) compositions can be obtained by a process involving vacuum drying and freeze-drying. In a specific embodiment, the composition of the invention is formulated for delivery in the respiratory tract (e.g. by inhalation, intranasal or intrapulmonary route) in a spray-dried (see e.g. WO2010/135495) or droplet form (with a specific preference for droplets having an average diameter of 100-5000 μm).

The immunogenic combination, fusion polypeptide, nucleic acid molecule, vector, host cell or composition of the present invention is suitable for a variety of modes of administration. Any of the conventional administration routes are applicable in the context of the invention including systemic, topical or mucosal routes.

Systemic administration includes for example subcutaneous, intradermal, intramuscular, intravenous, intraperitoneal, intravascular, intraarterial injection as well as scarification. Injections can be made with conventional syringes and needles, or any other appropriate devices available in the art (e.g. electroporation). Mucosal administration includes without limitation oral/alimentary, intranasal, intratracheal, intrapulmonary, intravaginal or intra-rectal route. Administration in the respiratory tract can be performed through nebulisation or aerosolization of droplet, spray, or dry powdered compositions using appropriate dispenser. Topical administration can also be performed using transdermal means (e.g. patch and the like). Intramuscular, intradermal and subcutaneous routes are particularly preferred in the context of the invention as well as intranasal intratracheal and intrapulmonary administrations.

The appropriate dosage can be adapted as a function of various parameters, in particular the active agent(s) comprised in the composition, the mode of administration; the age, health, and weight of the subject; the nature and extent of symptoms; kind of concurrent treatment; the frequency of treatment; and/or the need for prevention or therapy. Further refinement of the calculations necessary to determine the appropriate dosage for treatment is routinely made by a practitioner, in the light of the relevant circumstances.

For general guidance, suitable dosage for a viral vector-comprising composition varies from about $10^4$ to about $10^{13}$ vp (viral particles), iu (infectious unit) or pfu (plaque-forming units) depending on the vector and the quantitative technique used. Techniques available to evaluate the quantity of vp, iu and pfu present in a sample are conventional in the art. For example, the number of adenoviral particles (vp) is usually determined by measuring the A260 absorbance or HPLC, iu titers by quantitative DBP immunofluorescence and pfu by counting the number of plaques following infection of permissive cells. Preferably, the vp/iu ratio is below 100 in accordance with FDA guidelines. A preferred dose contains from about $10^5$ to about $10^{12}$ vp of an adenoviral vector (e.g. about $5\times10^8$, about $10^9$, about $5\times10^9$, about $10^{10}$, about $5\times10^{10}$ vp or about $10^{11}$ vp). A dose from about $5\times10^5$ to about $10^9$ pfu are preferred for vaccinia (e.g. MVA)-based composition with a specific preference for about $5\times10^6$, about $10^7$, about $5\times10^7$, about $10^8$ or about $5\times10^8$ pfu. A dose from about $5\times10^4$ to about $10^7$ pfu are preferred for measles-based composition, with a specific preference for about $10^5$, $5\times10^5$, $10^6$ or $5\times10^6$ pfu. A composition based on plasmid vector may be administered in doses of between 10 μg and 20 mg, advantageously between 100 μg and 2 mg. A protein composition may be administered in doses of between 10 μg and 20 mg, with a special preference for about 0.1 mg to about 2 mg per kg body weight for each of the mycobacterial antigens comprised in the composition.

The administration may take place in a single dose or repeated doses after a certain time interval. Repeated administrations (2, 3, 4, 5, 6, 7, 8, 9, 10, etc) can be separated from each other by an appropriate period of time and carried out by the same route or by different routes of administration, either at the same site or at different sites. Moreover, each administration can use the same active agent(s) or different ones. For illustrative purposes, two or three subcutaneous administrations separated from each other by approximately one week (e.g. from 3 to 10 days) are particularly suitable for MVA-based compositions whereas one or two intramuscular administration(s) are particularly suitable for Ad-, measles- and plasmid-based compositions. It is also possible to proceed via sequential cycles of administrations (e.g. a cycle of weekly administrations) that are repeated after a rest period. The first series of administration(s) can be followed by one or more "recall" administration(s) (e.g. after 4 months to several years) so as to recall the primed anti-*Mycobacterium* immune response.

In a specific embodiment, the administrations can be carried out according to a prime boost modality which comprises sequential administrations of one or more priming composition(s) and one or more boosting composition(s). Typically, the priming and the boosting compositions use different active agents which comprise or encode at least a mycobacterial antigen, immunogenic domain or epitope in common. The priming and boosting compositions can be administered at the same site or at alternative sites by the same route or by different routes of administration. For example, compositions based on polypeptide can be administered by a mucosal route whereas compositions based on vectors are preferably injected, e.g. by subcutaneous or intramuscular route. For illustrative purposes, one may contemplate priming the host's response with a live attenuated bacterium (such as BCG) and boosting with at least one of the "active agent" described herein (e.g. the immunogenic combination, fusion polypeptide, nucleic acid molecule, vector (e.g. infectious viral particle), or host cell of the invention or any combination thereof).

Prophylactic and Therapeutic Use

The immunogenic combination, fusion(s), nucleic acid molecule, vector(s), host cell or composition of the invention is preferably for use for preventing or treating a *Mycobacterium* infection or any disease and pathologic condition caused by or associated with it. Such use aims at inducing or stimulating protective immune responses against a mycobacterial antigen/epitope.

In one embodiment, the immunogenic combination, fusion(s), nucleic acid molecule, vector, host cell or composition of the invention is for use in methods for preventing infection or delaying the risk of infection with a *Mycobacterium* in a subject in need thereof, especially a subject who has been in close contact with an infected individual having developed an active disease and thus at risk of developing a *Mycobacterium* infection (e.g. transmission by inhalation of bacilli in moist droplets coughed out by the individual with TB).

In another embodiment, the immunogenic combination, fusion(s), nucleic acid molecule, vector, host cell or composition of the invention is for use in methods for treating an active disease in a subject infected with a *Mycobacterium* species and especially Mtb, the method comprising the step of administering to the infected subject having developed an active disease, a therapeutically effective amount of the immunogenic combination, fusion(s), nucleic acid molecule, vector, host cell or composition described herein, so as to induce an immune response against the infecting *Mycobacterium* species, thereby delaying or reducing the risk of development of active disease.

An "active disease" refers to a *Mycobacterium* infection with manifested serious disease symptoms. For example, in a human subject, TB is characterized by general clinical signs (such as weight loss, asthenia, fever, night sweats), clinical signs and/or symptoms (such as cough, hemoptysis, thoracic pain in case of pulmonary TB), and/or in some cases extrapulmonary signs according to the sites of infection (such as lymph nodes, bone forms, meningitis, urologenital forms).

In still another embodiment, the immunogenic combination, fusion(s), nucleic acid molecule, vector, host cell or composition of the invention is for use in methods for preventing or treating reactivation in a subject latently-infected with a *Mycobacterium* species and especially *M. tuberculosis*, the method comprising the step of administering to said latently-infected subject, a therapeutically effective amount of the immunogenic combination, fusion(s), nucleic acid molecule, vector, host cell or composition described herein, so as to induce an immune response against the infecting *Mycobacterium* species, thereby preventing or delaying reactivation.

By "a latently infected subject" is understood an individual, who is already infected with a virulent *Mycobacterium* species (e.g. Mtb), but shows no manifested disease symptoms or clinical signs. Typically, the latently-infected subject retains the *Mycobacterium* within his bodies, is not clinically ill but retains a risk of subsequent progression to clinical disease (reactivation), particularly in the context of immunosuppression (e.g. co-infection with another pathogen such as HIV or under immunosuppressive treatment such as TNFa inhibitors). A Mtb latently-infected subject will be expected to be positive if tested by any test permitting the diagnosis of a Mtb infection (e.g. tuberculin test, Mantoux test for PPD reactivity, and/or IFNγ release assays).

The term "reactivation" refers to the later manifestation of disease symptoms of a *Mycobacterium*-associated disease in a subject who tests positive for a *Mycobacterium* infection but did not manifest apparent disease symptoms. For example reactivation may occur in an infected subject which may or may not have previously manifested active disease symptoms or who had been treated sufficiently to bring the infection into a latent state. For example, a Mtb-infected subject was previously immunized with BCG or previously treated for the Mtb infection (e.g. with one or more "front line" chemotherapeutic drug(s).

In a specific embodiment, the immunogenic combination, fusion(s), nucleic acid molecule, vector, host cell or composition of the invention is for use as BCG booster to increase efficacy of BCG vaccination in a vaccinated subject.

Association with Chemotherapy

The immunogenic combination, fusion(s), nucleic acid molecule, vector(s), host cell or composition of the invention may be employed in association with one or more conventional therapy, e.g. one or more chemotherapeutic drug(s) effective against a *Mycobacterium* infection (e.g. Mtb infection).

The chemotherapy is typically determined by the treating physician using current practice. Examples of such chemotherapeutic drugs include without limitation antibiotic(s) as well as small direct and indirect inhibitor molecules, antibodies and immunotherapeutics as described in the art. Typically, "front-line" antibiotic chemotherapy currently used to treat a Mtb infection that is not drug resistant includes isoniazid, rifamycins (i.e., rifampin, rifapentine and rifabutin), ethambutol, streptomycin, pyrazinamide and fluoroquinolones. "Second-line" chemotherapy used to treat a Mtb infection that has demonstrated drug resistance to one or more "first-line" therapy includes ofloxacin, ciprofloxacin, ethionamide, aminosalicylic acid, cycloserine, amikacin, kanamycin and capreomycin. The one or more chemotherapeutic(s) is/are generally administered over an appropriate period of time, for example, for one or several months (e.g. 1, 2, 3, 4, 5, 6, 9 or 12 months) or longer. Daily administration of doses 200 to 600 mg (e.g. 300 or 400 mg) over a period of time ranging from 6 to 12 months is appropriate.

In one embodiment, the immunogenic combination, fusion(s), nucleic acid molecule, vector, host cell or composition of the invention is for use for reducing the time course of chemotherapy against a *Mycobacterium* (e.g. Mtb) infection. Usually, administration of the active agent(s) described herein will allow to enhance the efficacy of chemotherapy, (e.g. decrease the duration and/or severity of the clinical signs, improve the sputum conversion rate, etc.), reduce the length of the chemotherapy and/or the number of chemotherapeutic drugs to be employed, especially when the infecting mycobacteria is drug resistant.

In accordance with the present invention, the immunogenic combination, fusion(s), nucleic acid molecule, vector, host cell or composition of the invention can be administered before, concurrently with, or after administration of the one or more chemotherapeutic drug(s). In one embodiment, the active agent described herein is administered at least 2 weeks after starting administration of the chemotherapy.

In a preferred embodiment, the immunogenic combination, fusion(s), nucleic acid molecule, vector, host cell and/or composition of the invention is for use for inducing or enhancing an immune response in the administered subject. Accordingly, the present invention also encompasses a method for inducing or stimulating an immune response against a mycobacterial antigen upon administration in a subject of the immunogenic combination, fusion(s), nucleic acid molecule, vector, host cell and/or composition of the invention.

The induced or stimulated immune response can be specific (i.e. directed to a mycobacterial epitopes/antigen) and/or non-specific (innate), humoral and/or cellular. In the context of the invention, the immune response is preferably a CD4+ or CD8+-mediated T cell response or both, directed to a mycobacterial antigen/epitope.

The ability of the active agents(s) described herein to induce or stimulate an immune response can be evaluated either in vitro or in vivo using a variety of direct or indirect assays which are standard in the art.

For example, induction of non-specific immunity can be performed by measurement of the NK/NKT-cells (e.g. representativity and level of activation), as well as IFN-related cytokine and/or chemokine producing cascades, activation of TLRs and other markers of innate immunity (e.g. Riano et al., 2012, Tuberculosis 92: 148-59).

The ability to stimulate a humoral response can be determined by an increase in antibody titer that is specific for at least one of the antigens comprised in or encoded by the immunogenic combination and fusion(s) described herein. Exemplary techniques include without limitation antibody binding, binding competition as well as ELISA and Western blot.

Evaluation of cellular immunity can be estimated for example by an increased frequency in immune cells such as T lymphocytes specific for at least one of the mycobacterial antigens comprised in or encoded by the immunogenic combination and fusion(s) described herein. One may also monitor cell proliferation upon radioactive labelling (e.g. T cell proliferation assays by [$^3$H] thymidine incorporation assay). Another and sensitive method for detecting the immune response is ELISpot in which the frequency of IFNγ-producing cells is determined. Cytotoxic capacity for antigen-specific T lymphocytes can also be evaluated in a sensitized subject or by immunization of appropriate animal models. It is also possible to proceed by quantification of the release of relevant Th1 and/or Th2 cytokine(s) produced by activated T cells using routine bioassays (e.g. by multiparameters flow cytometry (ICS), by cytokine profile analysis using multiplex technologies or ELISA, etc.). PCR techniques can also be used to determine the presence of mRNA coding for the relevant cytokines. It will be appreciated by a skilled person that a significant increase or decrease in the amount of such relevant cytokines can be used to assess the immunogenic activity of one or more of the active agent(s) described herein.

Such immunological read outs are acceptable correlate of protective immune response provided by the active agent(s) described herein against a *Mycobacterium* infection. A "Protective response" has its usual meaning, that the treatment provides a benefit to the treated subject as compared to the response in a non-treated subject; e.g. induction or stimulation of an immune response, protection from contracting a *Mycobacterium* infection, or increased resistance to an active disease or prevention against reactivation of a latent *Mycobacterium* infection or even curing after active disease development.

Such a protective immune response can also be evaluated in vivo in appropriate experimental animal, e.g. a mouse, a rat or a guinea pig (see Ashwin et al., 2008, Am J Resp, 39: 503-8; Acosta et al., 2011, Malays J Med, 18: 5-12), e.g. by measuring a reduction in mycobacterial colony-forming unit (cfu) from the spleen, lung or other tissue homogenates isolated from the animals which have received a challenge infection with a virulent strain of a *Mycobacterium* species (e.g. Mtb) after previously having been immunized with one or more of the active agent(s) described herein, as compared to the mycobacterial cfu in a control group of experimental animals infected with the same virulent strain of *Mycobacterium*, but which have not previously been immunized. The comparison between treated and non-treated groups can also be assessed on animal survival (an increased survival in the treated group will correlate with a protective immune response).

The protective response provided by the immunogenic combination, fusion(s), nucleic acid molecule, vector, host cell or composition of the invention can also be estimated upon administration in a human subject according to the modalities described herein, over the baseline status or over the expected status if not treated. The protective response can be evidenced by any relevant clinical measurement typically used by physicians or other skilled healthcare staff, including, for instance:

- A diminishment of disease incidence and/or prevalence and/or frequency in a given population such as the Chinese population or a population of migrants in a given country (e.g. a lower proportion of new individuals who have been diagnosed with a *Mycobacterium* infection or at risk of developing a *Mycobacterium* infection or a disease associated with a *Mycobacterium* infection in the group having received the active agent(s) described herein);
- A higher percentage of sputum conversion rate in the group of treated subjects;
- A higher percentage of curing active disease in the group of treated subjects;
- A diminishment of extent of *Mycobacterium* transmission after close contact with an infected subject (e.g. reduction or delay the risk of being infected or the risk of developing active disease and/or reduction or delay the risk reactivation in latently infected subjects);
- An amelioration of a disease state (e.g. decrease of bacterial cfu in a target tissue or in a biological sample; diminishment of the disease symptoms or their severity (e.g. number and/or severity of lesions in a target organ) or stabilized (not worsening) disease state); and
- An improved response of the treated subject to concurrent treatment (reduction of the need, number, duration and/or doses of conventional chemotherapeutic drugs).

In the context of the invention, the protective response can be transient (for a couple of weeks after cessation of administration) or sustained (for several months or years). As the natural course of clinical status which may vary considerably from a subject to another, it is not required that the protective response be observed in each subject treated but in a significant number of subjects (e.g. statistically significant differences between two groups can be determined by any statistical test known in the art, such as a Tukey parametric test, the Kruskal-Wallis test the U test according to Mann and Whitney, the Student's t-test, the Wilcoxon test, etc).

Such measurements can be performed before the administration of the active agent(s) described herein (baseline) and at various time points during treatment and at least for some (e.g. 12) weeks after cessation of the treatment.

For general guidance, a *Mycobacterium*-infection and associated disease can be detected by various means. For example, Mtb infection can also be oriented by a number of methods in clinical use today such as the Mantoux tuberculin skin test (TST), the Quantiferon test as well as in vitro detection of responses to HBHA (heparin binding haemagglutinin; Hougardy et al., 2007; PLos One 2(10): e926) or the detection of IP10 after stimulation in vitro with ESAT6, CFP10 and TB7.7 (Ruhwald et al., 2008; Microbes Infect 9: 806-12). Subjects developing an active disease may be diagnosed according to current practice. For illustrative purposes, TB diagnosis is based on detection of the causative bacterium in clinical specimens by microscopy, cultural techniques, polymerase chain reaction (PCR) and its various derivatives. DNA fingerprinting methods and spoligotyping can also be implemented. Mycobacterial culture is the gold standard method for identification of an isolate of the *Mycobacterium tuberculosis* complex and drug susceptibility testing. X ray techniques and clinical observations can also be implemented to support findings of active pulmonary and/or extrapulmonary disease. On the other hand, numerous serological assays have been developed for diagnosis of Mtb infection using a variety of antigens to detect circulating antibodies including complement fixation tests, haemagglutination tests, radio immunoassay and enzyme-linked immunosorbent assays (ELISA).

The present invention also relates to a method for the detection and/or quantification of antibodies directed to a *Mycobacterium* in a biological sample (e.g. plasma, serum, etc taken from a subject infected or susceptible to be infected by a *Mycobacterium*), which comprises the steps of bringing said biological sample into contact with a reagent comprising any of the immunogenic combination, fusion(s), nucleic acid molecules, vectors, infectious viral particles, host cells of the invention under conditions allowing the formation of a complex between the antibody and the mycobacterial antigen/epitope comprised or encoded by any of the above-cited reagents and detecting and/or quantifying the formation of said complex by any appropriate means. Detecting the presence of specific antibody is indicative of a *Mycobacterium* infection (e.g. Mtb).

A person skilled in the art will easily determine the quantity of reagent to be used in the methods of the invention. The means of detection and/or quantification of antigen/antibody complex are routine and well known to a person skilled in the art. By way of illustration, one may mention blots, ELISA, so-called sandwich techniques, competition techniques, and PCR techniques, in particular so called "real-time" techniques. The use of the above cited reagent can be facilitated by coupling (i.e., physically linking) to a detectable substance. Examples of detectable substances include various enzymes (e.g. horseradish peroxidase, alkaline phosphatase, beta-galactosidase or acetylcholinesterase), prosthetic groups (e.g. streptavidin/biotin, or avidin/biotin), fluorescent materials (e.g. umbelliferone, fluorescein, or fluorescein derivatives), luminescent materials, bioluminescent materials (e.g. luciferase, luciferin, or aequorin), and radioactive materials (e.g. $^{125}I$, $^{131}I$, $^{35}S$ or $^{3}H$).

The present invention also concerns a kit of reagents for diagnosis a *Mycobacterium* (e.g. Mtb) infection for antigen assay comprising the antibody of the invention and for antibody assay comprising the immunogenic combination, fusion(s), nucleic acid molecule, vector, host cell, composition of the invention.

All of the above cited disclosures of patents, publications and database entries are specifically incorporated herein by reference in their entirety to the same extent as if each such individual patent, publication or entry were specifically and individually indicated to be incorporated by reference.

Figure 1:
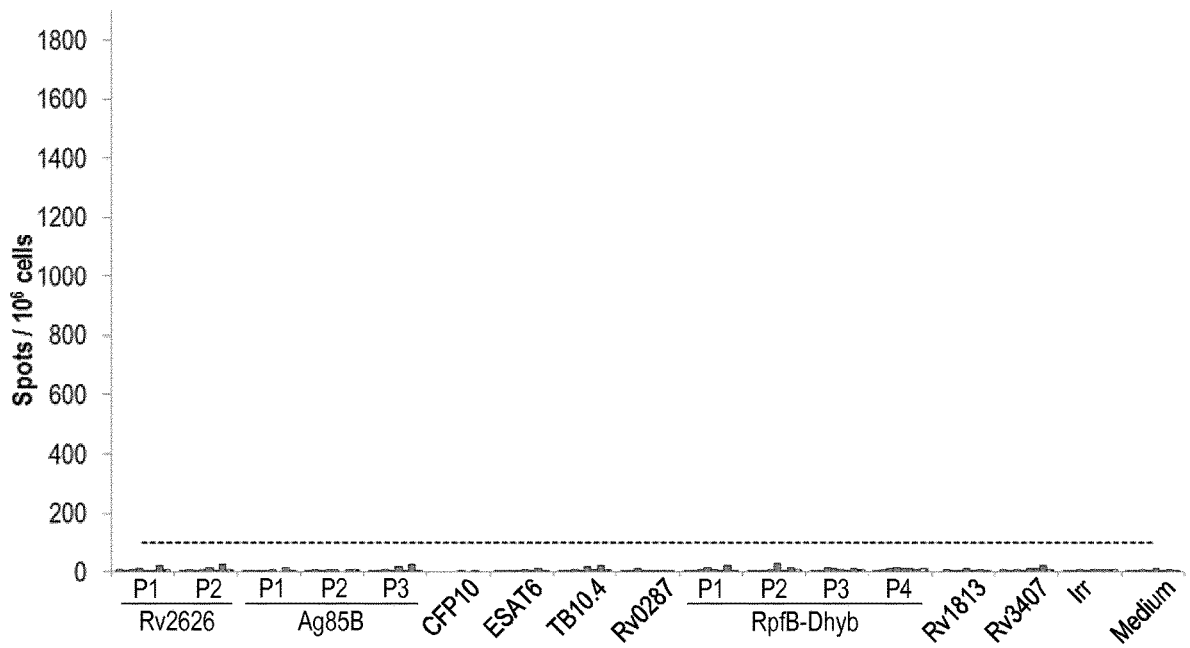
FIG. 1 illustrates the cellular immune response induced following immunization of C57BL/6 mice with (a) the empty MVATGN33.1 or (b) MVATG18379 (Rv2029-Rv2626-Rv1733-Rv0111+RpfB-Dhyb-Ag85B-TB10.4-ESAT6+Rv0569-Rv1813-Rv3407-Rv3478-Rv1807) or MVATG18598 (Rv2626-2a-Ag85B+CFP10-ESAT6+TB10.4-Rv0287+RpfB-Dhyb+Rv1813-2a-Rv3407). IFNγ-producing cells were evaluated one week following the last MVA injection by IFNγ ELISpot assays after ex vivo stimulation with specific peptide pools (P). Each plain bar represents response of individual mouse (6 mice/group) and hatched bars represent the median value of each group. Experimental cut-off is represented (dotted line). Statistical analysis was performed using a Mann-Whitney test. *, $p<0.05$.

FIG. 2 illustrates the cellular immune response induced following immunization of C57BL/6 mice with (a) the empty MVATGN33.1 or (b) MVATG18377 (Rv2029-Rv2626-Rv1733-Rv0111+RpfB-Dhyb-Ag85B-TB10.4-ESAT6+Rv0569-Rv1813-Rv3407-Rv3478-Rv1807) or MVATG18597 (ESAT6+CFP10+Rv2626+Ag85B+RpfB-Dhyb) or MVATG18633 (ESAT6+Rv1813+Rv2626+Ag85B+RpfB-Dhyb). IFNγ-producing cells were evaluated one week following the last MVA injection by IFNγ ELISpot assays after ex vivo stimulation with specific peptide pools (P). Each plain bar represents response of individual mouse (5 mice/group) and hatched bars represent the median value of each group. Experimental cut-off is represented (dotted line). Statistical analysis was performed using a Mann-Whitney test. *, $p<0.05$; **, $p<0.01$.

EXAMPLES

Materials and Methods

Vaccinia promoters and synthetic genes coding for the different Mtb antigens and fusions were synthesized by Geneart (Regensburg, Germany). The sequences were optimized for human codon usage and a Kozak sequence (ACC) was added before the ATG starting codon. Moreover some motives were excluded: TTTTTNT, GGGGG, CCCCC which are deleterious for expression in poxvirus vector and AAAGGG, AAAAGG, GGGAAA, GGGGAA, (and complementary sequences TTCCCC, TTTCCC, CCTTTT, CCCCTT) which can be deleterious for expression in some others vectors.

Construction of MVATG18598 Expressing Fusions of Heterooligomeric Mtb Antigens.

MVATG18598 contains 5 expression cassettes, each encoding a fusion of two Mtb antigens (as illustrated in Table 1). The first fusion Rv2626/2a/Ag85B (SEQ ID NO: 9) is constituted by the Rv2626 sequence from position 1 to 143, a GSG linker from position 144 to 146, the sequence of the self-cleaving peptide T2A from position 147 to 164 and the sequence of modified Ag85B (Ag85B modified with respect to the native counterpart by partial deletion of the N-terminal signal peptide, from the first residue to about position 32) from position 165 to 457. The nucleotide sequence encoding Rv2626/2a/Ag85B** (SEQ ID NO: 16) was placed under the control of the pB2R promoter (SEQ ID NO: 20). The second fusion (SEQ ID NO: 1) is a fusion of the two heterodimeric partners CFP10 and ESAT6. It is constituted by CFP10 from position 1 to 100, a 14 amino acid linker (corresponding to amino acids 149 to 162 of the Mtb protein Rv1827) from position 101 to 114 and ESAT6 from position 115 to 208. The nucleotide sequence encoding for CFP10/ESAT6 (SEQ ID NO: 13) was placed under the control of pH5R promoter (SEQ ID NO: 21). The third fusion (SEQ ID NO: 2) is a fusion of the two heterodimeric partners TB10.4 and Rv0287. It is constituted by TB10.4 from position 1 to 96, a 13 amino acid linker (corresponding to amino acids 149 to 161 of the Mtb protein Rv1827) from position 97 to 109 and Rv0287 from position 110 to 205. The nucleotide sequence encoding TB10.4/Rv0287 (SEQ ID NO: 14) was placed under the control of pSE/L promoter (SEQ ID NO: 22). The fourth fusion is the RPFB-Dhyb fusion described in SEQ ID NO: 8. It is a fusion between a RpfB antigen modified with respect to the native counterpart by deletion of the signal peptide (from the first residue to approximately residue in position 29), and by deletion of the catalytic domain, thus retaining RfpB from approximately position 30 to position 283 and the catalytic domain of the RpfD antigen with three mutations aimed at abolishing the associated enzymatic activity (E292K, T315A and Q347A). The nucleotide sequence encoding RPFB-Dhyb (SEQ ID NO: 15) was placed under the control of p7.5K promoter (SEQ ID NO: 23). The last fusion Rv3407/2a/Rv1813* (SEQ ID NO: 11) is constituted by Rv3407 from position 1 to 99, a GSG linker from position 100 to 102, the self-cleaving peptide E2A from position 103 to 122 and a modified Rv1813 (Rv1813*, modified with respect to the native counterpart by partial deletion of the N-terminal signal peptide, from the first residue to about position 31) from position 123 to 235. The nucleotide sequence encoding Rv3407/2a/Rv1813* (SEQ ID NO: 18) was placed under the control of pA35R promoter (SEQ ID NO: 24).

Two DNA fragments corresponding respectively to the first three expression cassettes and the last two expression cassettes, separated by suitable restrictions sites, were generated by synthetic way. After restriction by NotI and XhoI for the first fragment and by XhoI and PacI for the second fragment, both fragments were cloned in pTG18593 restricted by NotI and XhoI to give pTG18598.

The MVA transfer plasmid, pTG18593, is designed to permit insertion of the nucleotide sequence to be transferred by homologous recombination in deletion III of the MVA genome. It originates from the plasmid pUC18 into which were cloned the flanking sequences (BRG3 and BRD3) surrounding the MVA deletion III (Sutter and Moss, 1992, Proc. Natl. Acad. Sci. USA 89:10847).
Figure 1:
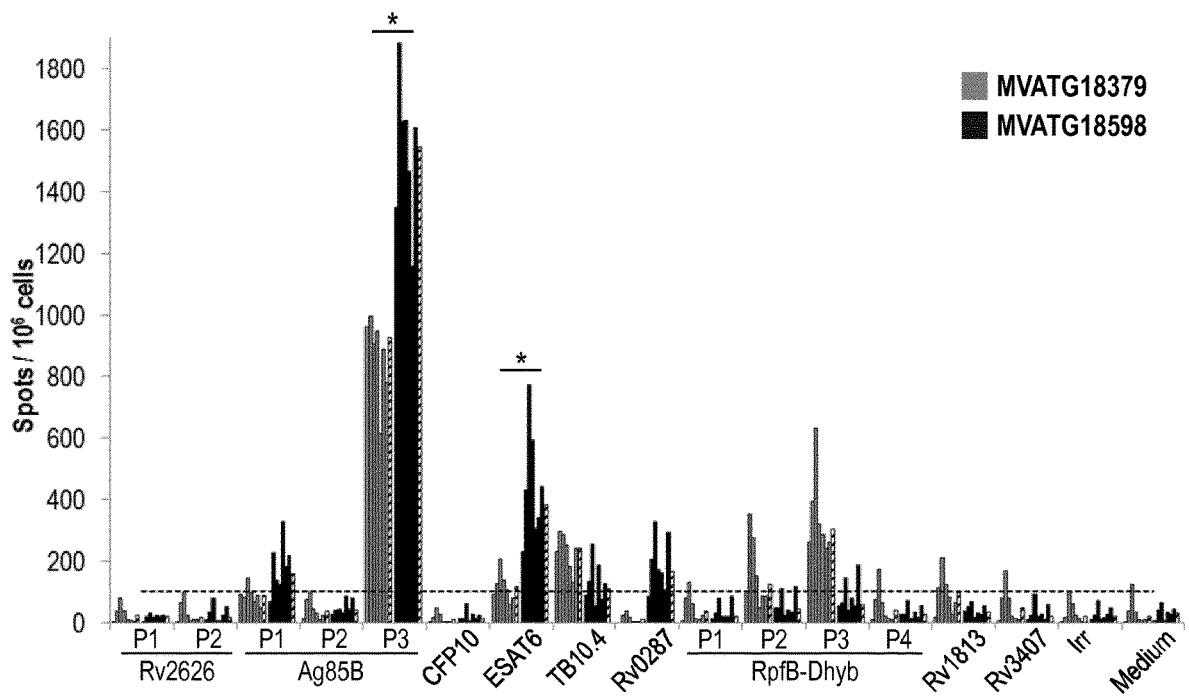
Figure 2:
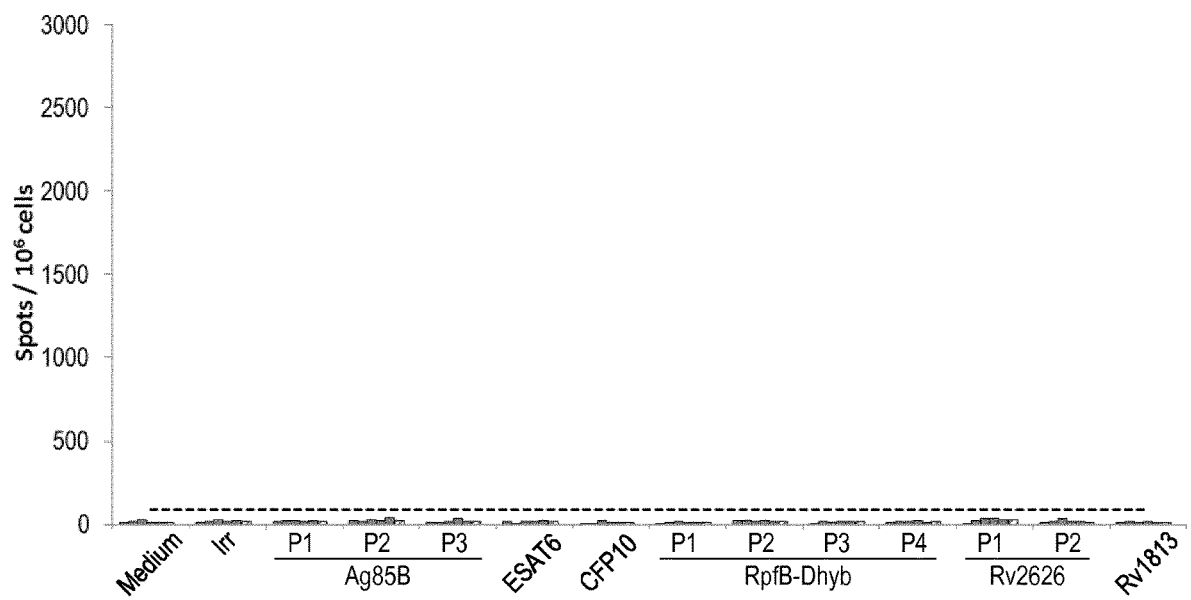
Figure 2:
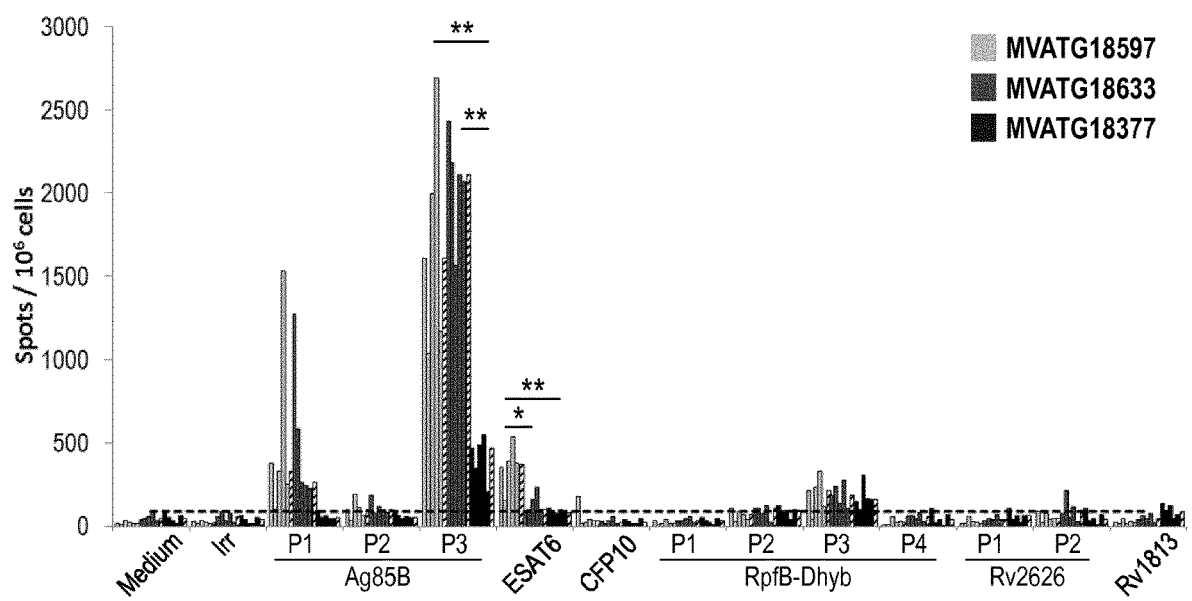

Generation of MVATG18598 was performed by homologous recombination in primary chicken embryos fibroblasts (CEF) infected with MVA and transfected by nucleofection with pTG18598 (according to Amaxa Nucleofector technology). Absence of contamination by parental MVA was verified by PCR.

Construction of MVA Vectors Co-Expressing Mtb Heterooligomeric Partners

Construction of MVATG18597

MVATG18597 contains 5 expression cassettes each encoding one Mtb antigen (Table 1). The nucleotide sequence encoding ESAT6 (SEQ ID NO: 25) was placed under the control of the pB2R promoter (SEQ ID NO: 20). The nucleotide sequence encoding for CFP10 (SEQ ID NO: 26) was placed under the control of pH5R promoter (SEQ ID NO: 21). The nucleotide sequence encoding Rv2626 (SEQ ID NO: 27) was placed under the control of pSE/L promoter (SEQ ID NO: 22). The nucleotide sequence encoding modified Ag85B (Ag85B*, modified with respect to the native counterpart by deletion of the N-terminal signal peptide, from the first residue to position 39) (SEQ ID NO: 28) was placed under the control of p7.5K promoter (SEQ ID NO: 23). The last antigen is a fusion polypeptide comprising the Mtb antigens RpfB and RpfD (e.g. as illustrated by the so-called RPFB-Dhyb of SEQ ID NO: 8). The nucleotide sequence encoding RPFB-Dhyb (SEQ ID NO: 15) was placed under the control of pA35R promoter (SEQ ID NO: 24).

A DNA fragment corresponding to the five expression cassettes separated by suitable restrictions sites and surrounded by around 30 bp of sequences homologous to the vaccinia transfer plasmid was generated by synthetic way. After restriction by SnaB1 and FspI the fragment was inserted by In-Fusion cloning (In-Fusion HD cloning kit, Clontech) in the vaccinia transfer plasmid pTG18593 digested by NotI and PacI, resulting in pTG18597.

Generation of MVATG18597 virus was performed in CEF by homologous recombination as described above.

Construction of MVATG18604

MVATG18604 contains 5 expression cassettes each encoding an individual Mtb antigen (Table 1). The nucleotide sequence encoding Rv0287 (SEQ ID NO: 29) was placed under the control of the pB2R promoter (SEQ ID NO: 20). The nucleotide sequence encoding for TB10.4 (SEQ ID NO: 30) was placed under the control of pH5R promoter (SEQ ID NO: 21). The nucleotide sequence encoding Rv3407 (SEQ ID NO: 31) was placed under the control of pSE/L promoter (SEQ ID NO: 22). The nucleotide sequence encoding Rv3478 (SEQ ID NO: 32) was placed under the control of p7.5K promoter (SEQ ID NO: 23) and the nucleotide sequence of Rv3477 (SEQ ID NO: 33) was placed under the control of pA35R promoter (SEQ ID NO: 24).

A DNA fragment corresponding to the five expression cassettes separated by suitable restrictions sites and surrounded by around 30 bp of sequences homologous to the vaccinia transfer plasmid was generated by synthetic way. After restriction by SnaB1 and FspI the fragment was inserted by In-Fusion cloning (In-Fusion HD cloning kit, Clontech) in the vaccinia transfer plasmid pTG18593 digested by NotI and PacI, resulting in pTG18604.

Generation of MVATG18604 virus was performed in CEF by homologous recombination as described above.

Production of Antibodies Against Mtb Antigens

Antibodies directed against the various Mtb antigens were produced following immunization of rabbits with a mixture of two different antigen-specific peptides (Eurogentec; Seraing, Belgium). Such peptides of 15 or 16 amino acid residues were selected after running epitope B prediction programs. Antisera against Rv1807, RPFB-Dhyb*, Rv1813* and Rv3407 antigens were generated following rabbits immunization with the two specific peptides at day 0 and three boosts at day 7, 10 and 18. Blood samples were taken before first peptide injection and at day 21. Final bleeding of rabbits was done at day 29. For Rv3478, the rabbits were injected at day 0, 22, 49 and 77 with the two specific 16 mer peptides. Blood samples were taken before first peptide injection and at day 31 and 59. Final bleeding of rabbits was done at day 87.

The final sera were evaluated by ELISA using the specific peptides and by Western-blot analysis using the individual Mtb gene expression plasmids.

Western Blot on MVA-Mediated Expression Products $4\times10^6$ CEF cells were infected at MOI 0.2 with the various MVA producing Mtb antigen fusions in presence or absence of proteasome inhibitor MG132 (10 μM) added to growth medium 30 min after infection. MVATGN33.1 empty vector was used as negative control. After 24 hours, medium was discarded and cells were lysed with 300 μL/dish of Tris-Glycin-SDS 2× buffer (ref: LC2676; Novex) supplemented with β-mercaptoethanol (5% v:v). The lysate was then sonicated and heated for 5 min at 95° C. Twenty microliters of cell lysates were submitted to electrophoresis onto precasted 4-15% Criterion gel using the Criterion Precast gel system (Biorad). Following electrophoresis, proteins were transferred onto a PVDF membrane (Trans-Blot® Turbo™ Transfer System (#170-4155, Biorad)). Immunodetection was performed with Mtb specific antibodies (see below). Immune-complexes were revealed using the ImmunStar WesternC kit (Biorad, ref 170.5070).

Sera (diluted 1/1000) obtained after immunization of rabbit, as described above, were also used for Western Blot detection of Rpf-B-D, Rv1813*, Rv3407 and Rv3478. Commercial antibodies were used for detecting ESAT6, Ag85B*, TB10.4 and Rv2626, respectively, mouse monoclonal antibody HYB076-08 (Santa-Cruz; # sc-57730, diluted 1/500) for ESAT6, rabbit polyclonal anti-serum NR-13800 (BEI, diluted 1/5000) for Ag85B*, mouse monoclonal antibody 26A11 (Lifespan-Biosciences; # LS-C91052 diluted 1/1000) for Rv2626 and polyclonal rabbit antibody ABIN361292 (Antibodies—online, diluted 1/1000) for TB10.4.

Solubility Analysis $4\times10^6$ CEF/well were cultivated in 6 wells plates as described above and infected by MVA at 0.2 MOI without MG132. Twenty four hours after infection, the culture medium was removed and cells lysed by 250 μL of either native buffer (50 mM Tris pH7.5; 150 mM NaCl; 1% tritonX100; Roche's antiprotease cocktail) or Novex buffer (Invitrogen) complemented with 0.7 M Beta-mercaptoethanol (Novex+BME).

Cell lysat was spun 16 000 g for 5 min at room temperature to remove cell debris and large protein aggregate. The pellet was resuspended in the original volume with 2504, of Novex+BME buffer. A western blot was performed on total cell (Novex condition), as well on pellet and supernatant to detect the expression of the antigen in the insoluble or soluble fractions respectively. The negative control was a lysat of cell infected with a MVA (N33) that does not carry any transgene. The control MVA allowed identifying any nonspecific background generated by the immunodetection.

If antigen or fusion was detected mainly in the soluble fraction, then 0.45-mL of lysat was fractionated on size exclusion chromatography (SEC) using S200 10/30 Superdex column equilibrated in PBS. 0.75 mL fractions were collected from 8-10 mL (void volume) to 23.6 mL (total volume of the column).

These fractions were analyzed by western blot with the specific antibodies or serum to determine the elution profile of each antigen or fusion. A fusion or an antigen was considered aggregated if it eluted in the void volume of the column.

Immunogenicity Evaluation in a Mouse Model
MVA Immunization Protocols

Immunogenicity of MVA TB candidates was evaluated in C57BL/6 mice. Each MVA vector was administered subcutaneously at the base of the tail twice, with a 4-week interval, at a dose of $1 \times 10^7$ pfu in 1004, of a Tris-HCl-buffered and sucrose-containing buffer. Cellular immune responses were evaluated 7 days after the last MVA injection by ELISpot IFNγ assay.

Peptide Libraries

A peptide library was used to restimulate ex-vivo the splenocytes from immunized mice. More precisely, peptides (15mers overlapping by 11 amino acids) covering all Mtb antigens contained in the constructions described above were synthetized (Proteogenix). Pools of peptides were prepared in DMSO with a final concentration of 1 μmol/L. One to four pools were needed so as to cover the full length of each Mtb antigen.

RpfB-Dhyb was covered by 4 pools of 24 peptides for the first 3 pools and 19 peptides for the fourth pool. Pool 1: 22 peptides covering RpfB residues 30 to 127; Pool 2: 22 peptides covering RpfB residues 117 to 215; Pool 3: 22 peptides covering RpfB residues 205 to 284 and RpfD residues 53 to 71; Pool 4: 21 peptides covering RpfD residues 61 to 153.

Rv1813 was covered by 1 pool of 25 peptides covering Rv1813 residues 34 to 143.

Rv3407 was covered by 1 pool of 22 peptides covering Rv3407 residues 1 to 99.

Rv2626 was covered by 2 pools of 17 and 16 peptides. Pool 1: 17 peptides covering Rv2626 residues 1 to 79; Pool 2: 16 peptides covering Rv2626 residues 69 to 143.

Ag85B was covered by 3 pools of 23 peptides. Pool 1: 23 peptides covering Ag85B residues 39 to 141; Pool 2: 23 peptides covering Ag85B residues 131 to 233; Pool 3: 23 peptides covering Ag85B residues 223 to 325.

ESAT-6 was covered by 1 pool of 21 peptides covering ESAT-6 from residues 1 to 95.

CFP10 was covered by 1 pool of 23 peptides covering CFP10 from residues 1 to 100.

TB10.4 was covered by 1 pool of 21 peptides covering TB10.4 from residues 1 to 96.

Rv0287 was covered by 1 pool of 22 peptides covering Rv0287 from residues 1 to 97.

IFNγ ELISpot Assays

Splenocytes from immunized mice were collected and red blood cells were lysed (Sigma, R7757). $2 \times 10^5$ cells per well were cultured in triplicate for 40 h in Multiscreen plates (Millipore, MSHA S4510) coated with an anti-mouse IFNγ monoclonal antibody (BD Biosciences; 10 μg/mL, 551216) in αMEM culture medium (Gibco, 22571) supplemented with 10% FCS (JRH, 12003-100M), 80 U/mL penicillin/80 μg/mL streptomycin (PAN, P06-07-100), 2 mM L-glutamine (Gibco, 25030), 1x non-essential amino acids (Gibco, 11140), 10 mM Hepes (Gibco, 15630), 1 mM sodium pyruvate (Gibco, 31350) and 50 μM. β-mercaptoethanol (Gibco, 31350) and in presence of 10 units/mL of recombinant murine IL2 (Peprotech, 212-12), alone as negative control, or with:

The above-described pool of peptides at a final concentration of 1 μmol/L
5 μg/ml of Concanavalin A (Sigma, C5275) for positive control.
Irrelevant peptide IFNγ-producing T cells were quantified by ELISpot (cytokine-specific enzyme linked immunospot) assay as previously described (Himoudi et al., 2002, J. Virol. 76: 12735-46). Results are shown as the mean value obtained for triplicate wells. An experimental threshold of positivity for observed responses (or cut-off) was determined by calculating a threshold value which corresponds to the mean value of spots observed with medium alone+2 standard deviations, reported to $10^6$ cells. A technical cut-off linked to the CTL ELISpot reader was also defined as being 50 spots/$10^6$ cells (which is the value above which the CV (coefficient of variation) of the reader was systematically less than 20%). The highest cut-off value between technical and experimental cut-offs is represented on figures. Only responses (median value for each group of mice) above cut-off are considered as positive. Statistical analyses of ELISpot responses were conducted by using a Kruskal-Wallis test followed, when a significant difference was obtained, by a Mann-Whitney test. P value equal or inferior to 0.05 will be considered as significant.

Results

Example 1: Generation of a Recombinant MVA Expressing Fusions of Heterodimeric Partners MVATG18598 MVA was engineered so as to express two fusions of heterodimeric partners ESAT6 with CFP10 and TB10.4 with Rv0287 (also named TB9.8) together with three fusions of additional mycobacterial antigens involving latent (Rv2626, Rv3407 and Rv1813), active (Ag85B) and resuscitation (RPFB-Dhyb) Mtb antigens. A flexible linker of 13 to 14 amino acids was added between each partner to favor the folding of the heterodimers. In some case, sequences coding for self-cleaving peptides 2A were added between the two elements of the fusion to allow the synthesis of both elements separately. Two different peptides 2A were used in the constructs: T2A (from *Thosea asigna* virus) and E2A (from *Equine rhinitis* A virus). Altogether, MVATG18598 contains five independent expression cassettes driving by five different promoters (as illustrated in Table1).

MVATG18597 and MVATG18604 were generated as controls co-expressing (non-fused configuration) heterodimeric partners ESAT6 and CFP10 (MVATG18597) and TB10.4 and Rv0287 as well as Rv3478 and Rv3477 (MVATG18604) together with other additional latent (Rv2626, Rv3407 and Rv1813), active (Ag85B) and resuscitation (RPFB-Dhyb) Mtb antigens MVA.

More specifically,
MVATG18598 contains 5 fusions of 10 Mtb antigens, respectively Rv2626/2a/Ag85B** under the control of pB2R promoter, CFP10/ESAT6 under the control of pH5R promoter, RPFB-Dhyb under the control of of p7.5K promoter, TB10.4/TB9.8 under the control pSE/L promoter and Rv3407/2a/Rv1813* under the control of pA35R promoter.

MVATG18597 contains ESAT6 under the control of pB2R promoter, CFP10 under the control of pH5R promoter, Rv2626 under the control of pSE/L promoter, Ag85B* under the control of p7.5K promoter and RPFB-Dhyb under the control of pA35R promoter.

MVAT18604 contains Rv0287 under the control of pB2R promoter, TB10.4 under the control of pH5R promoter, Rv3407 under the control of pSE/L promoter, Rv3478 under the control of p7.5K promoter and Rv3477 under the control of pA35R promoter.

TABLE 1

| | Promoter and expression cassette | | | | |
|---|---|---|---|---|---|
| | pB2R | pH5R | pSE/L | P7.5K | pA35R |
| MVATG18597 | ESAT6 | CFP10 | Rv2626 | Ag85B* | RPFB-Dhyb |
| MVATG18604 | Rv0287 | TB10.4 | Rv3407 | Rv3478 | Rv3477 |
| MVATG18598 | Rv2626/2a/ Ag85B** | CFP10/ ESAT6 | TB10.4/ Rv0287 | RPFB-Dhyb | Rv3407/2a/ Rv1813* |

Example 2: Western Blot Analysis of MVA-Expressed Mtb Antigens and Fusions

CEF cells were infected (MOI 0.2) in the presence or absence of MG132, with the various MVA candidates described above and expression products were analyzed by Western blot under the conditions described in Materials and Methods. Immunodetection was performed with antibodies specific of the various Mtb antigens described herein, except for CFP-10, Rv0287 and Rv3477. Specifically, the sera obtained after immunization of rabbits (see Materials and Methods) were used for detection of Rv1807, RPFB-Dhyb*, Rv1813*, Rv3407, and Rv3478 whereas commercial antibodies were used for the detection of ESAT6, Ag85B*, TB10.4 and Rv2626.

The results were summarized in Table 2. Intense bands corresponding to the fusions of heterodimers CFP10/ESAT6 and TB10.4/Rv0287 were detected after immunodetection with anti-ESAT6 and anti-TB10.4 antibodies in the cell lysates originating from cells infected with MVATG18598. Bands resulting of the cleavage of peptide 2A were detected after immunodetection with anti-Rv2626 and anti-Ag85B* antibodies for the fusion Rv2626/2a/Ag85B**; and with anti-Rv3407 and anti-Rv1813 antibodies for the fusion Rv3407/2a/Rv1813*.

On the other hand, when expressed as individual antigens (MVATG18597 and MVATG18604), a faint band was detected with anti-ESAT6 antibody while no expression was detected with anti-TB10.4 antibody, in spite of the presence of their respective heterodimeric partner in the same vector. However, in both constructs, additional Mtb antigens were detected by immunodetection with the corresponding antibody. Indeed, a band corresponding to the expected size was detected after immunodetection with anti-Ag85B, anti-RPFB-Dhyb, anti-Rv2626, anti-Rv3478 and anti Rv3407 sera/antibodies.

TABLE 2

| MVA | Cassette | Ag detected | Expression level | MG132 effect |
|---|---|---|---|---|
| MVATG18597 | p7.5K-Ag85B* | Ag85B | + | neg |
| | pB2R-ESAT6 | ESAT6 | +/− | none |
| | pA35R-RPFB-Dhyb | RPFB-Dhyb | + | pos |
| | pSE/L | Rv2626 | +++ | neg |
| MVATG18604 | p7.5K-Rv3478 | Rv3478 | +++ | pos |
| | pH5R-TB10.4 | TB10.4 | − | na |
| | pSE/L-Rv3407 | Rv3407 | ++ | neg |
| MVATG18598 | pB2R-Rv2626/2a/ Ag85B** | Rv2626 | ++ | none |
| | | Ag85B | + | none |
| | pH5R-CFP10/ESAT6 | ESAT6 | +++ | neg |
| | p7.5K-RPFB-Dhyb | RPFB-Dhyb | + | none |
| | pSE/L-TB10.4/Rv0287 | TB10.4 | +++ | neg |
| | pA35R-Rv3407/2a/ Rv1813* | Rv3407 | +/− | pos |
| | | Rv1813 | + | pos |
| | | Rv1813 | ++ | neg | neg: best expression in absence of MG132
pos: best expression in presence of MG132
none: same expression in both conditions
na: not applicable

Example 3: Solubility Analysis of MVA-Expressed Mtb Antigens and Fusions

CEF infected with MVATG18598, MVATG18597 and MVATG18604, without MG132, were analyzed for the solubility of antigen or fusion. CFP10, Rv0287 and Rv3477 were not analyzed. Centrifugation at 16 000 g for 5 minutes allows the sedimentation of cell debris and large aggregates of protein (pellet comprising insoluble fraction). In contrast, the folded proteins and small aggregates remain in the supernatant (soluble fraction). The pellet was resuspended in the same volume as the supernatant and 5 to 15 μL of supernatant and resuspended pellet were loaded on SDS-PAGE. Therefore, the intensities of signal detected in "pellet" (P) and "supernatant "S" were directly comparable. Table 3 summarizes the results for each antigen or fusion expressed of the three MVA cited above.

TABLE 3

Solubility of antigen or fusion after centrifugation of cell lysat

| | MVATG18604 | MVATG18597 | MVATG18598 |
|---|---|---|---|
| Ag85B | na | 100 | 100 |
| Rv2626 | na | 100 | 100 |
| ESAT6 | na | 100 (weak signal) | 100 |
| TB10-4 | NED | na | 100 |
| RPFB-D | na | NED | 100 |
| Rv3407 | 100 | na | NED |
| Rv1813 | na | na | NED |
| Rv3478 | 50 | na | na |

Na: not applicable
NED: No Expression Detected
100%: antigen detected only in soluble fraction
>50%: antigen mainly detected in soluble fraction
50%: antigen detected in soluble and insoluble fraction with the same intensity
<50%: antigen mainly detected in insoluble fraction
0: antigen detected only in insoluble fraction For some antigens that were expressed mainly in the soluble fraction, a SEC of the soluble fraction was performed in order to evaluate the aggregation state of the antigens or fusion. The column used (i.e. Superdex 200

10/30) has a fractionation range, for globular protein, from 10 to 600 kDa. Any globular monomeric protein with a mass <600 kDa will elute after the void volume of the column. Therefore; any fusion or antigen eluting after the void volume was considered as not aggregated. The results are illustrated in Table 4

TABLE 4

Fraction of antigen not aggregated

| | MVATG18604 | MVATG18597 | MVATG18598 |
|---|---|---|---|
| Ag85B | na | 100 | 100 |
| Rv2626 | na | 100 | 100 |
| ESAT6 | na | ND | 100 |
| TB10-4 | na | na | 100 |
| RPFB-D | na | na | 50 |
| Rv3407 | ND | na | na |
| Rv1813 | na | na | na |
| Rv3478 | ND | na | na |

Na: not applicable
ND: Not done
100%: antigen detected only in fraction different of the void volume (not aggregated)
50%: antigen detected both in void volume (aggregated) and in fraction different of the void volume (not aggregated)

Summary of Solubility Results

Ag85B was detected at the expected size (not fused) and as a soluble protein in MVATG18597 and MVATG18598 infected CEF. In MVATG18598 infected CEF, faint bands corresponding to the size of the Ag85B uncleaved fusions were also detected. These bands were too faint to be analysed by SEC. SEC analysis demonstrated that Ag85B expressed by the two viruses mentioned above was folded protein.

Rv2626 was detected at the expected size (not fused) and as a soluble and folded protein in MVATG18597 and MVATG18598 infected CEF.

ESAT6 was barely detected when expressed unfused (MVATG18597) and was well detected when fused to CFP10 (MVATG18598). Interestingly, only the CFP10-ESAT6 fusion encoded by MVATG18598 was completely soluble and folded.

TB10-4 was not detected when expressed unfused (MVATG18604) and was well detected when fused to Rv0287 (MVATG18598). Interestingly, only the TB10-4-Rv0287 fusion encoded by MVATG18598 was completely soluble and folded.

RPFB-Dhyb was detected when expressed by MVATG18598 as a monomeric protein. RPFB-Dhyb expressed by MVATG18598 is soluble and SEC analysis demonstrated that RPFB-Dhyb protein was partially aggregated.

Rv3407 could not be detected in absence of MG132 in MVATG18598 infected CEF. Rv3407 is expressed as a complete soluble protein in MVATG18604 infected CEF. No analytical SEC was performed on the soluble fractions.
- Rv3478 is encoded by MVATG18604 as unfused protein. Rv3478 was detected only in the insoluble fraction or in both soluble and soluble fraction.
- Altogether, as illustrated with ESAT6 and TB10.4, fusion of a mycobacterial antigen with its natural heterodimeric partner permits to improve expression and solubility of the resulting gene product.

Example 4: Evaluation of the Immunogenicity of MVA Candidate Vaccines Expressing Mtb Antigens 4.1 Evaluation of Immunogenicity of MVATG18598 Candidate Vaccine Expressing Mtb Antigens in C57BL/6 Mice C57BL/6 mice were immunized twice at 4-week interval with either MVATG18379 (described in WO2014/009438) expressing 3 protein fusions «Rv2029-Rv2626-Rv1733-Rv0111+RpfB-Dhyb-Ag85B-TB10.4-ESAT6+Rv0569-Rv1813-Rv3407-Rv3478-Rv1807» or MVATG18598 expressing 5 different protein fusions «Rv2626-2a-Ag85B+CFP10-ESAT6+TB10.4-Rv0287+RpfB-Dhyb+Rv1813-2a-Rv3407». Specific cellular immune responses were evaluated one week after the last injection by IFNγ ELISpot assays following stimulation with peptide pools described herein. Mice were also immunized with empty MVA vector (MVATGN33.1) as a negative control.

As illustrated in FIG. 1*b*, both MVATG18379 and MVATG18598 induced IFNγ positive responses specific of Ag85B (Pool 3), ESAT6 and TB10.4 in C57BL/6 mice ranging from 113 to 1548 spots/$10^6$ cells. In addition, response specific of ESAT6 was significantly stronger with the MVATG18598 (387 spots/$10^6$ cells), expressing the ESAT6 partner CFP10, as compared with MVATG18379 (119 spots/$10^6$ cells) which does not express CFP10. Ag85B-specific response was also significantly higher when mice were injected with MVATG18598 as compared with the group vaccinated with MVATG18379 (1548 and 928 spots/$10^6$ cells, respectively). TB10.4-specific responses were similar between both groups vaccinated with either MVATG18379 or MVATG18598. RpfB-Dhyb specific response was detected only in mice vaccinated with MVATG18379. No signal specific of Rv2626, Rv1813 or Rv3407 was induced whatever the vaccine injected in C57BL/6 mice. As expected, no IFNγ response was detected in mice vaccinated with the empty MVATGN33.1 virus (FIG. 1*a*).

4.2 Evaluation of Immunogenicity of MVATG18597 and MVATG18633 Candidate Vaccines Expressing Mtb Antigens in C57BL/6 Mice C57BL/6 mice were immunized twice at 4-week interval with either MVATG18377 (described in WO2014/009438) expressing 3 protein fusions «Rv2029-Rv2626-Rv1733-Rv0111+RpfB-Dhyb-Ag85B-TB10.4-ESAT6+Rv0569-Rv1813-Rv3407-Rv3478-Rv1807», MVATG18597 expressing 5 individual Mtb antigens «Ag85B+ESAT6+CFP10+Rv2626+RpfB-Dhyb» or MVATG18633 encoding the same individual Mtb antigens excepted CFP10 as follows: «Ag85B+ESAT6+Rv1813+Rv2626+RpfB-Dhyb». Specific cellular immune responses were evaluated one week after the last injection by IFNγ ELISpot assays following stimulation with peptide pools, described herein, of shared Mtb antigens. Mice were also immunized with empty MVA vector (MVATGN33.1) as a negative control.

As illustrated in FIG. 2*b*, the three MVA-TB vaccines induced IFNγ positive responses specific of Ag85B (Pool 3), ESAT6 and RpfB-Dhyb in C57BL/6 mice ranging from 85 to 2113 spots/$10^6$ cells. In addition, response specific of ESAT6 was significantly stronger with the MVATG18597 (375 spots/$10^6$ cells), expressing the ESAT6 partner CFP10 protein, as compared with MVATG18377 and MVATG18633 (85 and 102 spots/$10^6$ cells, respectively) which do not express CFP10 protein. Ag85B-specific responses (Pools 1 and 3) were also significantly higher when mice were injected with MVATG18597 or MVATG18633 (from 262 to 2113 spots/$10^6$ cells) as compared with the group vaccinated with MVATG18377 (from 52 to 468 spots/$10^6$ cells). Rv1813 specific response was detected only in mice vaccinated with MVATG18377. Neither CFP10-nor Rv2626-specific signal was induced whatever the vaccine injected in C57BL/6 mice. As expected, no IFNγ response was detected in mice vaccinated with the empty MVATGN33.1 virus (FIG. 2*a*).

The invention claimed is:

1. A viral vector comprising:
a nucleic acid molecule encoding a fusion of the heterooligomeric mycobacterial antigens ESAT6 with CFP10, and
nucleic acid molecule(s) encoding one or more additional mycobacterial antigen(s) selected from the group consisting of Ag85B (Rv1886), RpfB, RpfD, Rv1813, Rv2626, Rv3407, and a mycobacterial antigen comprising an amino acid sequence as set forth in SEQ ID NO: 3 or 4.

2. The viral vector of claim 1, wherein said vector is a poxvirus vector selected from the group consisting of fowlpox, canarypox and vaccinia virus vector.

3. The viral vector according to claim 1 which is selected from the group consisting of:
(i) A viral vector comprising:
a) a nucleic acid molecule encoding a fusion comprising heterooligomeric mycobacterial antigens ESAT-6 and CFP10,
b) a nucleic acid molecule encoding Ag85B, and
c) a nucleic acid molecule encoding Rv2626; and
(ii) A viral vector comprising:
a) a nucleic acid molecule encoding a fusion comprising heterooligomeric mycobacterial antigens ESAT-6 and CFP10;
b) a nucleic acid molecule encoding a fusion comprising heterooligomeric mycobacterial antigens TB10.4 and TB9.8,
c) a nucleic acid molecule encoding a fusion polypeptide comprising the additional mycobacterial antigens Rv2626 and Ag85B;
d) a nucleic acid molecule encoding a fusion polypeptide comprising the additional mycobacterial antigens RpfB and RpfD; and
e) a nucleic acid molecule encoding a fusion polypeptide comprising the additional mycobacterial antigens Rv3407 and Rv1813.

4. The viral vector according to claim 1, wherein said nucleic acid molecules are placed under the transcriptional control of a one or more promoter(s) suitable for ensuring expression of the encoded fusion and additional mycobacterial antigen(s) in a mammalian cell.

5. A host cell comprising the viral vector according to claim 1.

6. A composition comprising at least one of the viral vector of claim 1 or at least one of the host cell of claim 5.

7. The composition of claim 6, wherein the composition further comprises a pharmaceutically acceptable vehicle.

8. A method for treating a *Mycobacterium* infection, or any disease and pathologic condition caused by or associated with such a *Mycobacterium* infection, in a subject in need thereof, comprising the step of administering a therapeutically effective amount of the composition of claim 6 to the subject.

9. A method for delaying the risk of infection with a *Mycobacterium* in a subject in need thereof, comprising the step of administering a therapeutically effective amount of the composition of claim 6 to the subject.

10. The method of claim 8, for treating an active disease in a subject infected with a *Mycobacterium* species.

11. The method of claim 8, for treating reactivation in a subject latently infected with a *Mycobacterium*.

12. The method of claim 8, wherein the subject has previously been immunized with Bacille-Calmette-Guerin (BCG).

13. The method of claim 8, further comprising the administration of one or more chemotherapeutic drug(s) effective against a *Mycobacterium* infection.

14. The method of claim 8, for inducing or enhancing an immune response in the administered subject.

15. The method of claim 14, wherein said induced or stimulated immune response is a CD4+ and/or CD8+-mediated T cell response directed to a mycobacterial antigen/epitope.

16. The viral vector according to claim 1, further comprising nucleic acid molecule(s) encoding a fusion of the heterooligomeric mycobacterial antigens TB10.4 (Rv0288) with TB9.8 (Rv0287).

17. The viral vector according to claim 1, further comprising nucleic acid molecule(s) encoding one or more other additional mycobacterial antigen(s).

18. The viral vector according to claim 1, wherein said vector comprises a nucleic acid molecule encoding a fusion of the heterooligomeric mycobacterial antigens ESAT6 with CFP10, and
   a) nucleic acid molecule(s) encoding mycobacterial antigens Rv2626 and Ag85B; or
   b) a nucleic acid molecule(s) encoding a fusion of the heterooligomeric mycobacterial antigens TB10.4 and TB9.8 and nucleic acid molecule(s) encoding mycobacterial antigens Rv2626, Ag85B, RpfB, RpfD, Rv3407 and Rv1813.

19. The viral vector according to claim 1, wherein said additional mycobacterial antigen(s) are encoded in the form of separate polypeptides and/or in the form of fusion of two.

20. The viral vector according to claim 19, wherein said fusion polypeptide of additional mycobacterial antigens comprises (i) Rv2626 and Ag85B, (ii) RpfB and RpfD, or (iii) Rv3407 and Rv1813.

21. The viral vector according to claim 20, wherein said fusion polypeptide of additional mycobacterial antigens comprises:
   a) one or more peptide(s) to ensure appropriate folding of said mycobacterial antigens such as a protease cleavage site inserted between the upstream and downstream polypeptides of said fusion polypeptide; or
   b) an amino acid sequence exhibiting at least 70% identity with any of the amino acid sequences shown in SEQ ID NO: 8 to SEQ ID NO: 12.

22. A composition comprising at least one viral vector according to claim 21.

23. A method of treating a *Mycobacterium* infection in a subject in need thereof, comprising administering a therapeutically effective amount of a composition comprising the vector of claim 21 to the subject.

* * * * *